United States Patent [19]

Pestka et al.

[11] Patent Number: 4,503,035

[45] Date of Patent: Mar. 5, 1985

[54] PROTEIN PURIFICATION PROCESS AND PRODUCT

[75] Inventors: Sidney Pestka, North Caldwell, N.J.; Menachem Rubinstein, Rimon, Israel

[73] Assignee: Hoffmann-La Roche Inc., Nutley, N.J.

[21] Appl. No.: 465,979

[22] Filed: Feb. 14, 1983

Related U.S. Application Data

[60] Continuation of Ser. No. 247,442, Mar. 25, 1981, abandoned, which is a division of Ser. No. 167,165, Jul. 9, 1980, Pat. No. 4,289,690, which is a continuation-in-part of Ser. No. 106,644, Dec. 26, 1979, abandoned, which is a continuation-in-part of Ser. No. 77,710, Sep. 21, 1979, abandoned, which is a continuation-in-part of Ser. No. 62,374, Jul. 31, 1979, abandoned, which is a continuation-in-part of Ser. No. 963,257, Nov. 24, 1978, abandoned.

[51] Int. Cl.$^3$ .................. A61K 45/02; C07C 103/52; C12P 21/00
[52] U.S. Cl. ................. 424/85; 260/112 R; 260/112.5 R; 435/68; 435/811
[58] Field of Search ............. 424/85, 112 R, 177; 260/112.5 R; 435/68

[56] References Cited

U.S. PATENT DOCUMENTS

| | | | |
|---|---|---|---|
| 3,144,390 | 8/1964 | Burke | 424/85 |
| 3,256,152 | 6/1966 | Lampson | 424/85 |
| 3,265,581 | 8/1966 | Fontes et al. | 424/85 |
| 3,385,757 | 5/1968 | Fenter et al. | 424/85 |
| 3,414,651 | 12/1978 | Fontes | 424/85 |
| 3,548,053 | 12/1970 | Joshi | 424/85 |
| 3,560,611 | 2/1971 | Chany et al. | 424/85 |
| 3,652,538 | 3/1972 | Niblock | 536/27 |
| 3,699,222 | 10/1972 | Issacs et al. | 424/85 |
| 3,773,924 | 11/1973 | Ho | 424/85 |
| 3,800,035 | 3/1974 | Goore | 424/85 |
| 3,804,826 | 4/1974 | Scheit et al. | 536/29 |
| 3,819,482 | 6/1974 | Vidaver et al. | 536/28 |
| 3,845,033 | 10/1974 | Harden | 536/29 |
| 3,910,824 | 10/1975 | Cartwright | 424/85 |
| 3,948,886 | 4/1976 | Shuman et al. | 536/29 |
| 3,970,749 | 7/1976 | Baugh | 424/85 |
| 3,975,344 | 8/1976 | Schwartz | 424/85 |
| 3,981,991 | 9/1976 | Steuart et al. | 424/89 |
| 4,017,600 | 4/1977 | Steuart et al. | 424/85 |
| 4,038,139 | 7/1977 | Birch | 424/85 |
| 4,041,152 | 8/1977 | Chany et al. | 424/85 |
| 4,060,457 | 11/1977 | Ilxanta | 424/85 |
| 4,061,538 | 12/1977 | Dormer et al. | 424/85 |
| 4,100,150 | 7/1978 | Cartwright | 424/85 |
| 4,130,641 | 12/1978 | Ts'o et al. | 536/29 |
| 4,144,126 | 3/1979 | Burkedge | 424/85 |
| 4,168,261 | 9/1979 | Edy | 424/85 |
| 4,462,940 | 7/1984 | Hanisch et al. | 424/85 |

OTHER PUBLICATIONS

Berg, K., et al., J. Immunoly, vol. 114, pp. 640-644, 1975.
Lin, L., et al., Fed. Proc. Fed. Am. Soc. Exp. Biol., vol. 37, p. 1441, 1978.
Knight, Jr., E., Proc. Nat. Acad. Sci., vol. 73, pp. 520-523, 1976.
Berthold, W., et al., J. Biol. Chem., vol. 253, pp. 5206-5212, 1978.
Karvakita, M., et al., J. Biol. Chem., vol. 253, pp. 598-602, 1978.
Iwakura, Y., et al., J. Biol. Chem., vol. 253, pp. 5074-5079, 1978.
Zoom, K., et al., Proc. Natl. Acad. Sci, vol. 76, pp. 5601-5605, 1979.
Torma, E., et al., J. Biol. Chem., vol. 254, pp. 4810-4816, 1976.
Chodha, K., et al., Biochemistry, vol. 17, pp. 196-200, 1978.
Davey, M. et al., J. Biol. Chem., vol. 28, pp. 7620-7625, 1976.
Jankowski, W., et al., J. Virology, vol, 16, pp. 1124-1130, 1975.
Braude, I., et al., Biochem. Biophys. Res. Comm., vol. 89, pp. 612-619, 1979.
Davey, M., et al., Biochemistry, vol. 15, pp. 704-713, 1976.
Reynolds, F., et al., Biochem. Biophys. Res. Comm., vol. 65, pp. 107-112, 1975.
Bridger, P., et al., J. Biol. Chem., vol. 252, pp. 6585-6587, 1977.
Rubinstein, M. et al., Proc. Natl. Acad. Sci., vol. 74, pp. 4969-4972, 1977.
K. Berg., "Sequential Antibody Chromatography of Human Leukocyte Interferon", Scand. J. Immunal. 6, 77-86, 1977.
K. Berg. et al., "Purification of Human Interferon . . . Anti-Interferon", Scand. J. Immunol., 8, 429-436, 1978.
K. Berg & I. Heron, "The Complete Purification of Human Leucocyte Interferon", Scand. J. Immunol., 11, 489-502, 1980.
K. Berg, "Purification & Characterization of Murine & Human Interferons," Acta Pathological, Microliologica et Immunologica Scandinavica, Section C, 1982 Supplement No. 279, (Munksgaard:Copenhagen) 75-76.

Primary Examiner—Blondel Hazel
Attorney, Agent, or Firm—Jon S. Saxe; George M. Gould

[57] ABSTRACT

An improved process for purifying proteins, particularly proteins having molecular weights in excess of 12,000 involves novel applications of high performance liquid chromatography on a preparative scale to provide homogeneous end product in excellent yield. In an embodiment of the process, human interferon is produced as a homogeneous protein.

14 Claims, No Drawings

PROTEIN PURIFICATION PROCESS AND PRODUCT

RELATED APPLICATIONS

This is a continuation of application Ser. No. 247,442, now abandoned, Mar. 25, 1981, which is a divisional of Ser. No. 167,165, filed 7/9/80, now U.S. Pat. No. 4,289,690, which is a continuation-in-part of Ser. No. 106,644 filed 12/26/79, now abandoned, which is a continuation-in-part of Ser. No. 77,710 filed 9/21/79, now abandoned, which is a continuation-in-part of Ser. No. 62,374 filed 7/31/79, now abandoned, which is a continuation-in-part of Ser. No. 963,257 filed 11/24/78. now abandoned.

BACKGROUND OF THE INVENTION

Purification of proteins has long been a problem in peptide chemistry. Techniques which have been employed include precipitation, gel filtration, ion exchange chromatography, gel electrophoresis, affinity chromatography, and many others too numerous to mention.

Schemes to isolate naturally occurring, high molecular weight proteins which are present in biological samples in extremely low concentrations have involved multi-step procedures utilizing assays of the aforementioned techniques. In a great number of such cases tremendous quantities of crude starting material must be accumulated and processed at high cost and usually with expenditure of great effort due to large losses of product in the later steps of the purification procedure.

A good case in point is the history of the numerous attempts to isolate and characterize interferon. Since its first discovery by Isaacs and Lindenmann in 1957, interferon whether of the leucocyte or fibroblast form has resisted the attempts of researchers at institutions throughout the world spanning over two decades to be isolated as a homogeneous peptide in amounts sufficient to allow characterization and identification of its specific biological and chemical properties.

In U.S. Pat. No. 3,699,222, which is directed to Isaacs and Lindenmann's original research with interferon, the purification of the active material is limited to ammonium sulfate precipitation followed by dialysis. Such procedures are relatively non-specific and thus the product obtained thereby is still in an extremely crude state.

A multi-step procedure for purifying interferon is disclosed in U.S. Pat. No. 3,414,651 utilizing selective adsorption on an amorphous, alumino-silicate, elution with iodine or thiocyanate solution, further precipitation of unwanted protein with aqueous HCl and then aqueous NaOH, precipitation of interferon from the basic solution with water-miscible solvents such as methanol, ethanol or acetone and finally chromatography of the redissolved interferon on an anion exchange resin such as DEAE cellulose to produce an interferon whose specific activity is indicated to have been enhanced 6,000 fold by the entire process. Specific interferons exemplified were chick and monkey interferon.

U.S. Pat. No. 3,800,035 describes a method for inducing interferon production in human leukocytes in the absence of serum. The leukocytes are primed with interferon, the serum removed by centrifugation, the white cells suspended in nutrient medium and induced with a suitable inducing agent. A similar disclosure for inducing interferon in cell cultures is provided in U.S. Pat. No. 3,951,740 with the added feature of providing enough L-glutamine during the priming phase to keep the cells in an active metabolic state.

A further purification variation is taught in U.S. Pat. No. 3,975,344 where a crude human fibroblast interferon solution derived from the incubation medium of the cell culture was purified by zonal density gradient ultracentrifugation. This technique was indicated to give higher yields and purification than obtained with the conventional procedure of column chromatography on Sephadex G-100.

Recent scientific papers directed to the purification and attempted characterization of interferons can be summarized as follows:

Knight, E. (1976) "Interferon: Purification and Initial Characterization from Human Diploid Cells," Proc. Natl. Acad. Sci. U.S.A. 73, 520–523.

Torma, E. T., and Paucker, K. (1976) "Purification and Characterization of Human Leukocyte Interferon Components," J. Biol. Chem. 251, 4810–4816.

Bridgen, P. J., Anfinsen, C. B., Corley, L., Bose, S., Zoon, K. C., Ruegg, U. Th., and Buckler, C. E. (1977) "Human Lymphoblastoid Interferon, Large Scale Production and Partial Purification," J. Biol. Chem. 252, 6585–6587.

DeMaeyer, J., Tovey, M. G., Gresser, I., and DeMaeyer, E. (1978) "Purification of Mouse Interferon by Sequential Affinity Chromatography on poly(U) and Antibody-agorose columns," Nature 271, 622–625.

Kawakita, M., Cabrer, B., Taira, H., Rebello, M., Slattery, E., Weideli, H., and Lengyel, P. (1978) "Purification of Interferon from Mouse Ehrlich Ascites tumor cells," J. Biol. Chem. 253, 598–602.

Berthold, W., Tan, C., and Tan, Y. H. (1978) "Purification and in vitro labeling of interferon from a human fibroblastoid cell line," J. Biol. Chem. 253, 5206–5212.

Jankowski, W. J., Davey, M. W., O'Malley, J. A., Sulkowski, E., and Carter, W. A. (1975) "Molecular Structure of Human Fibroblast and Leukocyte Interferons: Probe by Lectin- and Hydrophobic Chromatography," J. Virology 16, 1124–1130.

Davey, M. W., Sulkowski, E., and Carter, W. A. (1976) "Hydrophobic Interaction of Human, Mouse, and Rabbit Interferons with Immobilized Hydrocarbons," J. Biol. Chem. 251, 7620–7625.

Chadha, K. C., Sclair, M., Sulkowski, E., and Carter, W. A. (1978) "Molecular Size Heterogeneity of Human Leukocyte Interferon," Biochemistry 17, 196–200.

While several of the above papers contain claims to have purified mouse or human interferons to homogeneity none of the classical proofs of homogeneity of protein material were given nor were any properties of the allegedly pure compounds described.

The use of high performance liquid chromatography for purification of proteins is generally known in the art. These references specifically describe ion exchange and size exclusion type columns in protein purification. See for example Regnier and Noel, J. Chromatog. Sci. 14, 316 (1976) and Chang et al., Anal. Biochem. 48, 1839 (1976).

The use of LiChrosorb RP-18 (octadecyl bound silica microparticle column) in reverse phase partition chromatography was successfully employed to purify peptides such as β-endorphin. Rubinstein et al. Proc. Natl. Acad. Sci., U.S.A. 74, 4969 (1977).

The partial characterization of three species of mouse interferons (MW=33,000; 26,000 and 20,000) is described by Cabrer et al., J. Biol. Chem. 254 (10); 3681 (1979).

DESCRIPTION OF THE INVENTION

The present invention relates to improved processes for purifying proteins. In particular, it has been discovered that proteins having molecular weights greater than about 12,000 can be purified with high resolution and high yield on a preparative scale by utilizing one or more high pressure liquid chromatography steps with columns containing a porous silica matrix to which octyl groups are bonded and columns containing a porous silica matrix to which glyceryl groups are bonded. These columns, which can be used sequentially and under varying conditions of pH and organic solvent gradient, offer the capability to purify to homogeneity protein materials that are present in extremely small quantities in cell extracts or growth media.

In a preferred specific embodiment of the present invention, the novel purification process is employed to purify interferon to homogeneity in amounts sufficient to allow chemical characterization of this medicinally valuable substance for the first time. The ability to chemically characterize interferon represents a significant advance in the development of this substance since it now allows the compound to be prepared either by conventional peptide synthesis procedures or alternatively by synthesizing the DNA corresponding to the interferon amino acid sequence and introducing such DNA into a suitable organism by DNA-recombinant techniques. The resulting organism will then have the capability of producing interferon which can be scaled up by application of fermentation techniques to provide a convenient source of this heretofore scarce compound on a commercial level.

The irregularly shaped, totally porous silica microparticle columns (particle size=10 microns; average pore size=100 Å) having octyl or glyceryl groups bound thereto used in the practice of the invention are articles of commerce identified respectively by the trademarks LiChrosorb RP-8 and LiChrosorb Diol. They are available from EM Laboratories of Elmsford, N.Y. Equivalent columns identified as Chromegabond C-8 (octyl) columns are available from E.S. Industries, Marlton N.J.

Other columns which can also be utilized for purposes of the present invention include cyanopropyl, cyclohexyl, phenyl and octadecyl bonded silica columns.

A convenient high pressure liquid chromatography system for utilizing the aforesaid columns is described in U.S. Pat. No. 4,116,046, inventor Stanley Stein.

In performing the instant process the solution of the impure high molecular weight peptide, preferably in aqueous buffer at a pH compatible with the properties of the protein in question, is passed through the silica matrix column. Usually the procedure is carried out under pressure, preferably in the range of from about 50 to about 5,000 psi. The protein is adsorbed into the column and is then subsequently eluted in selective fashion using a gradient of an aqueous water miscible solvent. Suitable water miscible solvents for this purpose include alkanols such as n-propanol, 2-propanol, ethanol, methanol, tert-butanol and the like, or cyclic ethers such as dioxane. Fractionation of the eluate is accomplished by utilizing fraction collectors in a manner known per se with concomitant monitoring of the protein content in each fraction by peptide monitors operating at high sensitivity. A suitable system for this purpose is disclosed by Bohlen et al., Anal. Biochem. 67, 438 (1975). It is also desirable to monitor the presence of the target protein by a suitable bioassay.

The decision as to whether to employ both the octyl bonded glyceryl bonded silica matrix columns and if so what order to select depends in large part on the nature of the protein to be purified. It has been found, for example, that in the specific case of human leukocyte interferon best results are achieved by initially resolving the impure interferon solution through the octyl bonded silica matrix column using a buffer pH of about 7.5 and elution with a gradient of increasing n-propanol concentration then passing the collected active fractions through the glyceryl bonded silica matrix column in 0.1M sodium acetate and eluting with a gradient of decreasing n-propanol and finally passing the separated interferon components through the octyl bonded silica matrix column in a 1M pyridine-2M formic acid system and eluting using an increasing n-propanol gradient. In this manner, each of the three separate forms of human leukocyte interferon can be resolved into separate, sharp peaks representing the homogeneous proteins. The overall purification starting with the incubation medium to the second octyl bonded silica matrix chromatography step was 60,000 to 80,000 fold while the cumulative yield through the glycerol bonded silica matrix chromatography step ranged from 30 to 50%.

The homogeneous human leukocyte interferon species obtained by the practice of the process of the invention each exhibited a sharp peak on the aforesaid high performance liquid chromatographic column and a single narrow band on sodium dodecyl sulfate(NaDodSO$_4$)polyacrylamide gel electrophoresis in the presence of 2-mercaptoethanol. Extraction of the gel gave a single sharp peak of antiviral activity coinciding with the protein band. The specific activity of the pure interferon species was found to be in the range of about $0.9-4.0 \times 10^8$ with MDBK bovine cells and in the range of about $2 \times 10^6 - 7.6 \times 10^8$ with the AG1732 human cell line. The molecular weights ranged from about 16,000 to 24,000 as seen in Table 4 and subsequently.

Interferons have exhibited antiviral, antitumor, growth inhibition and immunosuppression activity. These activities have been obtained even at the clinical level using $1-10 \times 10^6$ units daily with relatively crude preparations, less than 1% of which was human interferon. The purified, homogeneous interferons which are an aspect of the invention can be utilized in the same manner as the previously employed crude preparations with adjustments in the dosage to provide the desired level of interferon units. The individual species can be utilized per se or alternatively mixtures of two or more of such species can be employed. Such mixtures can be obtained by mixing the isolated species as desired or stopping the purification procedure where several species of interferon are present but no non-interferon active proteins are present so that the composition is a mixture of homogeneous interferon proteins.

The aforesaid purification process, while exemplified by the case of human leukocyte, can also be employed to purify other interferons including human fibroblast interferon and interferons from other animal sources as well as other proteins having molecular weights of greater than about 12,000. Thus, for example, pro-opiocortin (MW ca 30,000) has been purified to homogeneity using the procedures of the present invention. See Kimura et al., Proc. Nat'l. Acad. Sci. USA 76 (4), 1756 (1979). It is within the skill of the art to select the proper specific conditions to provide the optimum resolution for each different type of protein to be purified.

The various species of human leukocyte interferon purified to homogeneity have been found to contain some common tryptic peptides which have the following amino acid sequences:

(1) . . . Ala-Glu-Ile-Met-Arg . . .
(2) . . . Tyr-Phe-Gln-Arg . . .
(3) . . . Ile-Thr-Leu-Tyr-Leu-Lys . . . , and
(4) . . . Thr-Leu-Met-Leu-Leu-Ala-Gln-Met-Arg . . .

The procedures of the process aspect of the invention allowed the purification to homogeneity of separate interferon species and the comparison of these various species. It was found that all species have a closely related structure since their amino acid compositions are similar. Peptide mapping revealed more structural data. Thus, species $\alpha_1$, $\alpha_2$, $\beta_1$ and $\beta_2$ were almost indistinguishable based on the peptide profile, whereas significant differences were observed among all other species. Such differences cannot be explained by a difference only in the saccharide portion of the molecule. Since the heterogeneity was observed even in a preparation from a single leukemic patient, one must conclude that there is more than one structural species of human leukocyte interferon. The heterogeneity results from differences in primary amino acid sequence. In addition, however, other posttranslational modifications such as glycosylation and cleavages may contribute to the heterogeneity.

It is already known in the art that cell free translation of human leukocyte interferon MRNA in the presence of glycosylation inhibitors produces a biologically active interferon. Thus, since the sugar moiety does not appear to be needed for human leukocyte interferon to exhibit its biological activity, it is within the scope of the present invention to purify the interferon produced by recombinant DNA microorganisms containing the human leukocyte gene to homogeneity. As indicated above some heterogeneity in amino acid sequence can be expected between interferons derived from different source cells without affecting the underlying biological equivalence of these human leukocyte interferons. Thus a variation in one of the amino acids of one or more of the tryptic peptides or a total heterogeneity in the full amino acid sequence of up to 15% or the presence or absence of glycosylation will not affect equivalency of the human leukocyte interferon peptides for the purposes of this invention.

It is clear that several of the species ($\alpha_2$, $\beta_1$, $\gamma_1$ and $\gamma_2$) have a blocked $NH_2$ terminus, whereas species $\alpha_1$ and $\beta_2$ are essentially unblocked. The nature of the blocking group has not yet been determined. Nevertheless, differences in the $NH_2$ terminus represent additional variations among the species.

The process and product aspects of this invention are further illustrated by reference to the following Examples.

EXAMPLE 1

Homogeneous Human Leukocyte Interferon

Human Leukocyte Interferon Production and Assay

Human leukocytes were isolated from the buffy coat fraction of whole blood from normal donors and used for the induction of interferon with Newcastle disease virus. Casein was substituted for serum to provide a simple environment from which to isolate the interferon. Interferon titers were determined by a cytopathic effect-inhibition assay that is performed within 16 hr. This assay is described in detail in U.S. patent application Ser. No. 963,257, filed Nov. 24, 1978, entitled Improved Interferon Assay, inventors, Familletti et al. All interferon titers are expressed in terms of reference units/ml or units/mg calibrated against a reference standard for human leukocyte interferon (G-023-901-527) provided by the National Institute of Health.

Details of the induction and concentration of human leukocyte interferon are as follows:

A. Preparation of Leukocytes:
  Materials:
    Human white cell fractions, collected aseptically.
    0.83% ammonium chloride
    Hydroxyethyl starch (HES) a commercial blood thickener (6%)
    Minimal Essential Medium, Eagle's (MEM) (Gibco #109)
    Penicillin-Streptomycin Solution (PS) (Gibco #514)
    0.4% trypan blue solution.
  G forces given herein are average g values.
  Procedure:
    1. Remove white cells from 10 four-part blood bags aseptically to a graduated cylinder and note the volume.
    2. Combine cells and HES in a 1-liter separatory funnel at a volume ratio of 2:1. (2% final concentration of HES)
    3. Mix thoroughly and allow to stand 1 hour at room temperature.
    4. Remove the lower fraction (red cells) and discard.
    5. Collect the upper fraction (white cells) into centrifuge tubes.
    6. Centrifuge upper fraction 500×g for 15 min, 4° C.
    7. Decant the supernatant containing HES.
    8. Replace decanted HES with an equal volume of 0.83% NH$_4$Cl (room temperature) swirling the tube gently to resuspend the cells. Note: If clumping occurs, aspirate cells with a pipet several times to break up clumps.
    9. Allow cells to stand 5 min at room temperature.
    10. Centrifuge cells at 500×g for 10 min, 4° C.
    11. Decant the NH$_4$Cl solution and resuspend the cells as in step 8 with another volume of fresh 0.83% NH$_4$Cl.
    12. Allow cells to stand 5 min at room temperature. Note: At this point all white cells from the 10 blood bags should be combined into a single centrifuge bottle.
    13. Centrifuge cells at 500×g for 10 min, 4° C.
    14. Decant supernatant and discard.
    15. Resuspend cells in approximately 1/5 of the final working volume in MEM supplemented with 1% penicillin-streptomycin solution.
    16. Count the white cells.
      (a) Make a 1:100 dilution in 0.4% trypan blue and count cells with the aid of a hemacytometer; or
      (b) count cells with an electronic cell counter.

B. Preparation of Newcastle disease virus concentrate.
  Materials:

Commercially grown and harvested Newcastle disease virus (NDV), unconcentrated (8 L)
Dulbecco's phosphate buffered saline (PBS) without calcium and magnesium (sterile) (2 L)
70% ethanol (2 L)
Sterile distilled water (4 L)

Procedure:
1. Centrifuge unconcentrated NDV at 1500×g for 1 hour to clarify fluid.
2. Pool supernatants; discard pellets.
3. Centrifuge pooled supernatants using continuous flow ultracentrifuge (Electronucleonics Model RK, J1 Rotor)
   (a) Purge inlet and outlet tubes and rotor of centrifuge with 2 L 70% ethanol. Drain rotor.
   (b) Purge with 4 L of sterile distilled water. Drain rotor.
   (c) Purge with 2 L of sterile PBS. Drain rotor.
   (d) Centrifuge pooled supernatants at a flow rate of 150 ml/min at 124,000×g (50,000 rpm)
4. Drain rotor and save (780 m).* Discard flow through.
5. Resuspend pellet (located at the base and lower side walls of the rotor) in 1/100 of the original starting volume in PBS.
6. Dispense concentrated virus in 1 ml lots and freeze quickly. Store at −70° C. or lower.

*Note: Rotor hold up (780 ml, step 4) contains virus and may be pooled with hold up from other runs and reconcentrated.

C. Determination of Hemagglutination titer of concentrated NDV.
Materials:
Freshly collected chicken blood (CRBC).
PBS as in part B.
Concentrated NDV prepared in part B.

Procedure:
1. Centrifuge fresh chicken blood at 500×g 30 min.
2. Decant serum and discard.
3. Resuspend cells in PBS, mix thoroughly, and centrifuge at 500×g for 10 min.
4. Decant PBS, add fresh PBS and centrifuge 500×g 10 min.
5. Decant PBS.
6. By using the packed cell volume, make a 1% suspension of the CRBC's in PBS.
7. Fill 12 consecutive wells of a 92-well microtiter plate (U-shaped wells) with 0.1 ml PBS.
8. Dilute concentrated NDV 1:100 in PBS.
9. Add 0.1 ml of the diluted virus to well #1.
10. Titrate 0.1 ml serially through well #12 (serial 2-fold dilutions).
11. Add 0.1 ml of the 1% CRBC suspension to each well.
12. Add 0.1 ml of the 1% CRBC suspension to 4 wells containing only 0.1 ml PBS. These wells serve as negative controls.
13. Read plate when CRBC's in control wells "button" in the bottom of the wells.

Notes:
(a) Titer is equal to the reciprocal of the highest dilution which interferes with normal "buttoning" of the CRBC's, expressed in hemagglutination units/ml (HA units/ml).
(b) In above procedure, well #1 represents a 1:400 dilution.
(c) A standard suspension of NDV of known titer is run with each unknown NDV titration to insure uniformity of the assay.

D. Preparation of Milk Casein.
Materials:
Skimmed Milk (0.05% fat) or Instant Dry Milk dissolved in water
MEM supplemented with 1% PS Procedure:
1. Autoclave the skimmed or reconstituted milk 10 min at 121° C. and 15 PSI.
2. Cool to room temperature. Milk should appear light tan in color and be homogeneous in appearance.
3. Centrifuge milk at 80,000×g for 90 min.
4. Discard supernatant and note volume.
5. Suspend the pellet in a volume equal to that of the discarded supernatant in MEM by stirring vigorously at 4° C. overnight.
6. Store casein solution at 4° C.

E. Induction of Human Leukocytes for Interferon Production with NDV and Concentration of Interferon.
Materials:
Human leukocytes free of red cell contamination as prepared in part A.
NDV concentrate as prepared in part B.
Casein solution as prepared in part D.
MEM supplemented with 1% PS
Induction vessel: a sterile, siliconized glass-tissue-culture-spinner flask, equipped with sampling port and magnetic stirring bar.
1N HCl
50% Trichloroacetic acid (TCA)
0.1M Sodium Bicarbonate
Human leukocyte interferon previously induced and concentrated by this method for priming.
Note: All containers and centrifuge bottles from this point on are to be polypropylene to minimize interferon adsorption.

Procedure:
1. To the induction vessel add:
   (a) washed leukocytes to a final concentration of $1 \times 10^7$ cells/ml;
   (b) casein solution to a final concentration of 10% (v/v);
   (c) human leukocyte interferon to a final concentration of 10 units/ml.
   (d) MEM to volume.
2. Mix contents gently.
3. Incubate induction vessel at 37° C. for 1 hour without stirring.
4. Add NDV to a final concentration of 15 HA units/ml.
5. Incubate induction vessel at 37° C. for 1 hour without stirring.
6. Incubate the induction vessel at 37° C. for 16–18 hours with enough stirring to gently suspend the cells.
7. Remove contents of induction vessel and centrifuge at 500×g for 15 min at room temperature. Discard pellet.
8. Acidify supernatant to pH 4.0 slowly with 1N HCl.
9. Hold for at least 2 hours at pH 4 at 4° C.
10. Centrifuge acidified material at 12,000×g for 10 min. Discard pellet (casein and virus). Remove a small sample of supernatant for assay.

11. Bring supernatant to 1.5% TCA slowly with 50% TCA. Let stand for at least 1 hour at 4° C.
12. Centrifuge precipitated interferon at 12,000×g for 10 min. Discrd supernatant.
13. Redissolve the interferon pellet with 0.1M sodium bicarbonate in approximately 1/200 of the original induction volume.
14. The solution was brought to 1% (weight/vol of Triton X-100 (a non-ionic detergent) and then acetic acid was added dropwise with stirring at 0° C., to a final concentration of 0.5M.
15. The mixture was stored at 0° C. for one hour and then for 16 hours at −20°.
16. The frozen material was then thawed and centrifuged (17,000×g, 10 min). The precipitate was discarded. The supernatant was brought to 4% (wt/vol) trichloroacetic acid at 0° C. and left 60 min at 0° C. The mixture was then centrifuged (12,000 g, 10 min, 0° C.) and the precipitate was dissolved in 0.5M sodium bicarbonate in approx. 1/2,000 of the original induction volume.

F. Gel Filtration

Solid urea is added to a concentration of 4M and the solution applied to a Sephadex G-100 fine column (2.6×90 cm) pre-equilibrated with a 4M urea-0.1M sodium acetate buffer. The column is eluted by the 4M urea-0.1M sodium acetate buffer (pH 7.5) at 0.5 ml/min at room temperature and 12.5 ml fractions are collected. Interferon activity was eluted in fractions #19–23.

High Performance Liquid Chromatography

Fractions #19–23 of the Sephadex G-100 run are combined and applied through the pump to a LiChrosorb RP-8,10μ column (4.6×250 mm) at 3,000 psi. The column is pre-equilibrated with a sodium acetate-acetic acid buffer (1M, pH 7.5) containing 0.01% v/v thiodiglycol. The column is washed with the same buffer (4 ml) and then eluted at 0.25 ml/min by a linear gradient of n-propanol (in the same buffer) from 0% to 20% (v/v) n-propanol in 1 hr and then linearly from 20 to 40% (v/v) n-propanol in 3 hr. Fractions of 0.75 ml. are collected and interferon elutes in fractions 23 to 40 from 25–30% n-propanol.

Fractions 27–33 containing most of the interferon activity from the LiChrosorb RP-8 chromatography are combined, n-propanol is added to a final concentration of 80% (v/v) and the solution is applied through the pump to a LiChrosorb Diol 10μ column (4.6×250 mm) at 3,000 psi. The column is pre-equilibrated with a sodium acetate (0.1M) buffer containing n-propanol (80% v/v). The column is washed with sodium acetate (0.1M)-n-propanol (80%) 4 ml, and then eluted at 0.25 ml/min by a 4 hr linear gradient from 72 to 50% (v/v) n-propanol. Fractions of 0.75 ml are collected and the activity eluted as three distinct major peaks. The first, labelled α, elutes at 68% n-propanol. The second, labelled β, elutes at 66.5% n-propanol. The third, labelled γ, elutes at 65.5% n-propanol. The total recovery of interferon activity is better than 80%.

The fractions comprising each peak were pooled separately and purified individually through subsequent steps. Since peak γ was present in high abundance and appeared to be better resolved from other components, it was selected for further purification. Fractions 54–56, comprising peak γ from the Diol column, were pooled and n-propanol was removed by two extractions with an equal volume of n-hexane. Traces of hexane were removed under a stream of nitrogen. Pyridine and formic acid were added to final concentrations of 1M and 2M, respectively, and the solution was applied to a LiChrosorb RP-8 column (10μ; 4.6×250 mm) previously equilibrated with 1M pyridine and 2M formic acid (pH 4.0). The column was eluted with a linear 20 to 40% (v/v) n-propanol gradient in the 1M pyridine-formate buffer in 3 hours at a flow rate of 0.2 ml/min. Fractions of 0.6 ml. were collected. The major peak of activity coincided with a protein peak. Fractions 45–46 (32% n-propanol) comprising this peak were combined and rechromatographed under similar conditions. Interferon was eluted in fraction 31 (32% n-propanol). The specific activity of this fraction was calculated to be $4 \times 10^8$ units/mg. in relation to bovine serum albumin. This material was used for further characterization. The fluorescence profiles of the high performance steps were so remarkably reproducible that they provided a continual fingerprint of the entire procedure.

The results of the purification are summarized in Table 1. The overall purification starting with the incubation medium to the second RP-8 column was 60,000- to 80,000-fold. The cummulative yield from step 1 through the Diol step ranged from 30 to 50%. Beyond this step, each of the three species of interferon was purified separately.

TABLE 1

PURIFICATION OF HUMAN LEUKOCYTE INTERFERON

| Step | Units Recovered × 10⁻⁶ | Protein Recovered (mg) | Relative Specific Activity (units/mg) | Degree of Purification | Recovery Range Per Step (%) |
|---|---|---|---|---|---|
| 1. Incubation medium | 50 | 10,000 | $5 \times 10^3$ | 1 | — |
| 2. pH 4 Supernatant | 50 | 2,000 | $2.5 \times 10^4$ | 5 | 100 |
| 3. 1.5% Trichloroacetic acid percipitate | 40 | 1,000 | $4 \times 10^4$ | 8 | 80–100 |
| 4. Triton X-100/Acetic acid supernatant | 40 | 250 | $1.6 \times 10^5$ | 32 | 70–100 |
| 5. 4% Trichloroacetic acid precipitate | 35 | 175 | $2 \times 10^5$ | 40 | 80–90 |
| 6. Sephadex G-100 | 32 | 57 | $5.6 \times 10^5$ | 112 | 70–90 |
| 7. Lichrosorb RP-8 (pH 7.5) | 28 | 11 | $2.5 \times 10^6$ | 500 | 80–100 |
| 8. Lichrosorb Diol | | | | | |
| Peak α | 11 | 1.1 | $1 \times 10^7$ | 5,000 | |
| Peak β | 2.5 | N.D. | N.D. | N.D. | 70–90 |
| Peak γ | 12.5 | 0.21 | $6 \times 10^7$ | 12,000 | |
| 9. Lichrosorb RP-8 (pH 4) | 1.6 | 0.0064 | $3 \times 10^8$ | 60,000 | 40–60 |

TABLE 1-continued
PURIFICATION OF HUMAN LEUKOCYTE INTERFERON

| Step | Units Recovered $\times 10^{-6}$ | Protein Recovered (mg) | Relative Specific Activity (units/mg) | Degree of Purification | Recovery Range Per Step (%) |
| --- | --- | --- | --- | --- | --- |
| 10. Lichrosorb RP-8 (pH 4) | 8.2 | 0.021 | $4 \times 10^8$ | 80,000 | 40-60 |

For determination of protein recovered in each fraction, bovine serum albumin was used as a standard. The absolute specific acitivity determined by amino acid analysis of the homogeneous peak of step 10 was found to be $2 \times 10^8$ units/mg (see text). Step 9 was performed on Peak γ of Step 8. Step 10 was performed on pooled material from Step 9 of several preparations. "N.D." represents "not determined".

Polyacrylamide Gel Electrophoresis

Samples of interferon ($1.5 \times 10^5$ units) were incubated in NaDodSO$_4$ and 2-mercaptoethanol and then applied to a slab gel. After electrophoresis, a single sharp band was obtained upon staining with Coomassie blue. The apparent molecular weight was estimated to be 17,500 in comparison with standard proteins. The gel was then cut into 1 mm slices. Each slice was homogenized in 0.4 ml of 0.5M NaHCO$_3$ and 0.1M NaDodSO$_4$ and assayed for interferon activity. A single peak of antiviral activity was obtained coinciding with the single protein band. No other peak of activity was observed.

Amino Acid Analysis

Amino acid analysis of homogeneous human leukocyte interferon (peak γ) was performed with the fluorescamine amino acid analyzer on 0.5–1 μg samples of native and S-carboxymethylated interferon. For measurement of cysteine/cystine ratio, native interferon was carboxymethylated and then hydrolyzed in 6N HCl under reducing conditions (0.1% thioglycolic acid). Under these conditions, cysteine is measured as S-carboxymethylcysteine whereas cystine is measured as free cysteine. Amino acid analyses are summarized in Table 2. The specific activity based on amino acid content was found to be $2 \times 10^8$ units/mg.

TABLE 2
AMINO ACID COMPOSITION OF HUMAN LEUKOCYTE INTERFERON

| Amino Acid | Residues |
| --- | --- |
| Asx | 15.2 ± 0.2 |
| Thr* | 7.5 ± 1.5 |
| Ser* | 8.0 ± 0.5 |
| Glx | 24.0 ± 1.6 |
| Pro | 6.3 ± 1.3 |
| Gly | 5.5 ± 0.5 |
| Ala | 8.2 ± 0.2 |
| Cys (total) | 3.3 ± 0.7 |
| ½ Cystine+ | 1.8 ± 0.2 |
| Cysteine+ | 1.5 ± 0.5 |
| Val | 7.8 ± 1.2 |
| Met | 3.9 ± 0.2 |
| Ile | 8.9 ± 0.9 |
| Leu | 21.8 ± 1.8 |
| Tyr | 5.1 ± 0.4 |
| Phe | 9.1 ± 0.3 |
| His | 3.3 ± 0.4 |
| Lys | 11.6 ± 1.6 |
| Arg | 7.3 ± 1.5 |
| Trp** | 0.7 ± 0.5 |

*Corrected to time 0
+Measured after carboxymethylation of native interferon
**Measured after hydrolysis in methanesulfonic acid (4M)

EXAMPLE 2
Homogeneous Human Leukocyte Interferon from Leukocytes of Leukemic Patients Human Leukocyte Interferon Production and Assay:

Human leukocytes were isolated from the blood of leukemic patients (chronic myelogenous leukemia) by leukapheresis and used for the induction of interferon with Newcastle disease virus. Casein was substituted for serum to provide a simple environment from which to isolate the interferon. Interferon titers were determined by a cytopathic effect-inhibition assay that is performed within 16 hr. This assay is described in detail in U.S. patent application Ser. No. 963,257 filed Nov. 24, 1978, entitled Improved Interferon Assay, inventors Familletti et al. All interferon titers are expressed in terms of reference units/ml or units/mg calibrated against a reference standard for human leukocyte interferon (G-023-901-527) provided by the National Institutes of Health.

Details of the Induction and concentration of human leukocyte interferon are as follows:

Abbreviations Used
  AO—1% ammonium oxalate sterile filtered
  P-S—Penicillin/streptomycin Gibco #514
  MEM—Minimal Essential medium-F 11 Gibco #109
  HEPES—N-2-hydroxyethylpiperazine-N'-2-ethane-sulfonic acid
All solutions sterile
All solutions equilibrated to 37° C. prior to use A. Preparation of Newcastle disease virus concentrate.
  Materials:
    Commercially grown and harvested Newcastle disease virus (NDV), unconcentrated (8 L)
    Dulbecco's phosphate buffered saline (PBS) without calcium and magnesium (sterile) (2 L)
    70% ethanol (2 L)
    Sterile distilled water (4 L)
  Procedure:
    1. Centrifuge unconcentrated NDV at 1500×g for 1 hour to clarify fluid.
    2. Pool supernatants; discard pellets.
    3. Centrifuge pooled supernatants using continuous flow ultracentrifuge (Electronucleonics Model RK, J1 Rotor)
      (a) Purge inlet and outlet tubes and rotor of centrifuge with 2 L 70% ethanol. Drain rotor.
      (b) Purge with 4 L of sterile distilled water. Drain rotor.
      (c) Purge with 2 L of sterile PBS. Drain rotor.
      (d) Centrifuge pooled supernatants at a flow rate of 150 ml/min at 124,000×g (50,000 rpm)

4. Drain rotor and save (780 ml).* Discard flow through.
5. Resuspend pellet (located at the base and lower side walls of the rotor) in 1/100 of the original starting volume in PBS.
6. Dispense concentrated virus in 1 ml lots and freeze quickly. Store at −70° C. or lower.

*Note: Rotor hold up (780 ml, step 4) contains virus and may be pooled with hold up from other runs and reconcentrated.

B. Determination of Hemagglutination titer of concentrated NDV.
Materials:
Freshly collected chicken blood (CRBC).
PBS as in part B.
Concentrated NDV prepared in part B.
Procedure:
1. Centrifuge fresh chicken blood at 500×g 30 min.
2. Decant serum and discard.
3. Resuspend cells in PBS, mix thoroughly, and centrifuge at 500×g for 10 min.
4. Decant PBS, add fresh PBS and centrifuge 500×g 10 min.
5. Decant PBS.
6. By using the packed cell volume, make a 1% suspension of the CRBC's in PBS.
7. Fill 12 consecutive wells of a 92-well microtiter plate (U-shaped wells) with 0.1 ml PBS.
8. Dilute concentrated NDV 1:100 in PBS.
9. Add 0.1 ml of the diluted virus to well 190 1.
10 Titrate 0.1 ml serially through well #12 (serial 2-fold dilutions).
11. Add 0.1 ml of the 1% CRBC suspension to each well.
12. Add 0.1 ml of the 1% CRBC suspension to 4 wells containing only 0.1 ml PBS. These wells serve as negative controls.
13. Read plate when CRBC's in control wells "button" in the bottom of the wells.
Notes:
(a) Titer is equal to the reciprocal of the highest dilution which interferes with normal "buttoning" of the CRBC's, expressed in hemagglutination units/ml (HA units/ml).
(b) In above procedure, well #1 represents a 1:400 dilution.
(c) A standard suspension of NDV of known titer is run with each unknown NDV titration to insure uniformity of the assay.

C. Preparation of Milk Casein.
Materials:
Skimmed Milk (0.05% fat) or Instant Dry Milk dissolved in water
MEM supplemented with 1% PS
Procedure:
1. Autoclave the skimmed or reconstituted milk 10 min at 121° C. and 15 PSI.
2. Cool to room temperature. Milk should appear light tan in color and be homogeneous in appearance.
3. Centrifuge milk at 80,000×g for 90 min.
4. Discard supernatant and note volume.
5. Suspend the pellet in a volume equal to that of the discarded supernatant in MEM by stirring vigorously at 4° C. overnight.
6. Store casein solution at 4° C.

D. Preparation of Leukocytes
1. Decant white cells from collection bag into a 650 or 500 ml. polycarbonate centrifuge bottle. If necessary in a separate centrifuge bottle, add remaining white cell and red cell suspension and process separately.
2. Add 2-3 volumes 0.9% saline (w/v).
3. Centrifuge 1500 RPM 14 min. in HS4 Rotor in Sorvall RC3. (g=430)
4. Aspirate supernatant.
*5. Resuspend cells in equal volume of AO by swirling gently.
6. Add an additional 3-5 times pellet volume of AO.
7. Mix gently and incubate a maximum of 15 min. at 37° C. Swirl intermittently.
8. Centrifuge as in step 3.
9. Aspirate supernatant.
10. If substantial red cell contamination is observed, repeat steps 5-9.

*use pipetting action only if necessary to resuspend cells and break down aggregates formed E. Induction of Interferon
1. Resuspend cells in a minimum of 5×volume of pellet with MEM.
2. Make 1:1000 fold dilution of cells in 0.4% trypan blue in PBS and count in Neuberger Hemocytometer. Count the 4 outer 4×4 cells and average. Each cell = $10^{-4}$ cc hence total cells is obtained by multiplication by factor of $10^7$ to achieve cells/ml.
*3. Set up cultures using following formulation per liter: about 800 ml. MEM: 90-100 ml. casein, 5 ml. P-S stock and 10 ml. of 1M HEPES. Fill culture flasks (BELLCO MODEL 1969-) to within 200-300 ml. of expected flask volume.
4. Add $10^{10}$ cells for each liter of final culture.
5. Wash walls and bring to final volume with MEM.
6. Incubate 30-45 min. with stirring at 37°.
7. Add stock NDV to achieve 15 HA units/ml.
8. Stir 5 min.
9. Incubate 1 hr. without stirring 37°.
10. Incubate overnight with stirring.

*Culture flasks are usually established prior to production run.

F. Concentration and Fractionation of Interferon
1. Spin 11 min. at 4500 RPM in the HS4 Rotor of the Sorvall RC3 centrifuge (g=3900).
2. Cool supernatant in ice/water.
3. Bring to pH 4.0 with 1.0N HCl (ca. 25 mL 1.0N HCl/liter culture).
4. Let stand 2 hrs in ice to allow resultant precipitate to settle.
5. Decant supernatant by pumping through 3μ PALL Filter (#SLK 7002 BPP).
6. Centrifuge remaining sludge for quantitative recovery of acidified culture broth.
7. Add to previous filtered supernatant.
8. Add TCA to supernatant to 1.5% w/v ([TCA]-stock=50% w/v; use 31 ml TCA stock/Liter supernatant).
9. Let stand to settle minimum 24 hrs.
10. Jar vessel to promote sedimentation of precipitate on vessel walls.
11. Pump off supernatant.
12. Spin the suspension at 6000 RPM for 15-20 min. in the GS-3 Sorvall Rotor. Discard supernatant.
13. Dissolve pellet in 0.1N $NaHCO_3$ in as small a volume as possible.

14. Bring the solution to 1% (w/v) of Triton X-100 (a non-ionic detergent) and then add acetic acid dropwise with stirring at 0° C., to a final concentration of 0.5M. Store one hour at 0° C.

15. The mixture was centrifuged (17,000×g, 10 min., 0° C.). The precipitate was discarded. The supernatant was brought to 4% (w/v) trichloroacetic acid at 0° C. and left 60 min. at 0° C. The mixture was then centrifuged (12,000 g, 10 min., 0° C.) and the precipitate was dissolved in 0.5M sodium bicarbonate in approximately 1/2,000 of the original induction volume.

G. Chromatography

Gel Filtration

Solid urea is added to a concentration of 4M. and the solution applied to a Sephadex G-100 fine column (2.6×90 cm) pre-equilibrated with a 4M urea-0.1M sodium acetate buffer. The column is eluted by the 4M urea-0.1M sodium acetate buffer (pH 7.5) at 0.5 ml/min at room temperature and 12.5 ml fractions are collected. Interferon activity is eluted in fractions #19-23.

High Performance Liquid Chromatography

Fractions #19-23 of the Sephadex G-100 run are combined and applied through the pump to a Lichrosorb RP-8, 10μ column (4.6×250 mm) at 3,000 psi. The column is pre-equilibrated with a sodium acetate-acetic acid buffer (1M, pH 7.5) containing 0.01% v/v thiodiglycol. The column is washed with the same buffer (4 ml) and then eluted at 0.25 ml/min by a linear gradient of n-propanol (in the same buffer) from 0% to 20% (v/v) n-propanol in 1 hr and then linearly from 20 to 40% (v/v) n-propanol in 3 hr. Fractions of 0.75 ml are collected and interferon elutes at 25 to 30% n-propanol (fractions 23 to 40).

Fractions 27-33 containing most of the interferon activity from the Lichrosorb RP-8 chromatography are combined, n-propanol is added to a final concentration of 80% (v/v) and the solution is applied through the pump to a Lichrosorb Diol 10μ column (4.6×250 mm) at 3,000 psi. The column is pre-equilibrated with a sodium acetate (0.1M) buffer containing n-propanol (80% v/v). The column is washed with sodium acetate (0.1M)-n-propanol (80%), 4 ml, and then eluted at 0.25 ml/min by a 4 hr linear gradient from 72.5 to 50% (v/v) n-propanol. Fractions of 0.75 ml are collected and the activity eluted as three distinct major peaks. The first, labelled α, elutes at 68% n-propanol. The second, labelled β, elutes at 66.5% n-propanol. The third, labelled γ, elutes at 65.5% n-propanol. The total recovery is better than 80%.

The fractions comprising each peak were pooled separately and purified individually through subsequent steps. Fractions 43-46 comprising peak α from the Diol column were pooled and n-propanol was removed by two extractions with an equal volume of n-hexane. Traces of hexane were removed under a stream of nitrogen. Pyridine and formic acid were added to a final concentration of 1M and 2M respectively, and the solution was applied to a LiChrosorb RP-8 column (10μ 4.6×250 mm) previously equilibrated with 1M pyridine and 2M formic acid (pH 4.0). The column was eluted with a linear 20 to 40% (v/v) n-propanol gradient in the 1M pyridine-formate buffer in 3 hr at a flow rate of 0.2 ml/min. Fractions of 0.6 ml were collected. Interferon activity eluted as broad peaks in the range of 31 to 35% n-propanol. These fractions were combined and rechromatographed under identical conditions. Interferon was eluted in two main peaks $\alpha_1$ and $\alpha_2$ at 31 and 32% n-propanol. Minor components eluted by 34% n-propanol.

Fractions 47-50 comprising peak β from the Diol column were pooled. n-Hexane extraction was performed as described for peak α. Pyridine and formic acid were added to a final concentration of 1M and 2M respectively and the sample was chromatographed on LiChrosorb RP-8 as described for peak α. Interferon eluted in two main peaks: $\beta_2$ at 32% n-propanol and $\beta_3$ at 34% n-propanol. Rechromatography was not necessary in this case. In some preparations a peak designated $\beta_1$ eluting at 31% n-propanol was observed.

Fractions 52-54 comprising peak γ from the Diol column were pooled and processed as described for peaks α and β. The samples were chromatographed on LiChrosorb RP-8 as described for peak α. Interferon eluted in five peaks. The major peaks were: $\gamma_1$ at 31% n-propanol, $\gamma_2$ at 32% n-propanol, $\gamma_3$ at 34% n-propanol, $\gamma_4$ at 35% n-propanol and $\gamma_5$ at 35.5% n-propanol. Rechromatography was not necessary in this case.

The results of the purification to produce the individual species of interferon are summarized in Table 3.

TABLE 3

| Step | PURIFICATION OF LEUKOCYTE INTERFERON FROM CML CELLS | | | | |
|---|---|---|---|---|---|
| | Units Recovered $\times 10^{-6}$ | Protein Recovered mg | Specific** Activity units/mg | Degree of Purification | Recovery % |
| 1. Incubation medium | 800 | $20 \times 10^3$ | $4 \times 10^4$ | 1 | 100 |
| 2. pH 4 supernatant | 800 | $4 \times 10^3$ | $2 \times 10^5$ | 5 | 100 |
| 3. 1.5% trichloroacetic acid precipitate | 780 | $2 \times 10^3$ | $3.9 \times 10^5$ | 9.8 | 97 |
| 4. Triton X-100/acetic acid supernatant | 760 | 510 | $1.5 \times 10^6$ | 37.5 | 95 |
| 5. 4% Trichloroacetic acid precipitate | 810 | 350 | $2.3 \times 10^6$ | 57.5 | 100 |
| 6. Sephadex G-100 | 660 | 130 | $5.1 \times 10^6$ | 128 | 82 |
| 7. LiChrosorb RP-8 - pH 7.5 (two batches) | 510 | 26 | $2 \times 10^7$ | 500 | 64 |
| 8. LiChrosorb Diol | | | | | |
| Peak α | 149 | 5 | $3 \times 10^7$ | 750 | |
| Peak β | 148 | 3 | $5 \times 10^7$ | 1250 | |
| Peak γ | 139 | 1.7 | $8 \times 10^7$ | 2000 | |
| Total | 436 | | | | 54 |
| 9. LiChrosorb RP-8 - pH 4.0 | | | | | |
| Peak $\alpha_1$* | 9 | $35 \times 10^{-3}$ | $2.6 \times 10^8$ | 6500 | |
| Peak $\alpha_2$* | 26 | $65 \times 10^{-3}$ | $4.0 \times 10^8$ | 10000 | |
| Peak $\beta_2$ | 30 | $75 \times 10^{-3}$ | $4.0 \times 10^8$ | 10000 | |
| Peak $\beta_3$ | 13 | $32 \times 10^{-3}$ | $4.0 \times 10^8$ | 10000 | |
| Peak $\gamma_1$ | 15 | $58 \times 10^{-3}$ | $2.6 \times 10^8$ | 6500 | |

TABLE 3-continued

| | PURIFICATION OF LEUKOCYTE INTERFERON FROM CML CELLS | | | | |
|---|---|---|---|---|---|
| Step | Units Recovered $\times 10^{-6}$ | Protein Recovered mg | Specific** Activity units/mg | Degree of Purification | Recovery % |
| Peak $\gamma_2$ | 31 | $77 \times 10^{-3}$ | $4 \times 10^8$ | 10000 | |
| Peak $\gamma_3$ | 26 | $74 \times 10^{-3}$ | $3.5 \times 10^8$ | 8750 | |
| Peak $\gamma_4$ | 3.5 | $10 \times 10^{-3}$ | $3.5 \times 10^8$ | 8750 | |
| Peak $\gamma_5$ | 4.5 | $50 \times 10^{-3}$ | $0.9 \times 10^8$ | 2250 | |
| Total | 158 | | | | 20 |

*after rechromatography
**activity determined on MDBK (bovine) cells; protein measured with BSA as standard Species $\alpha_2$ and $\beta_2$ are further distinguishable by their elution characteristics on the LiChrosorb Diol column. As indicated above $\alpha_2$ elutes at 68% n-propanol and $\beta_2$ at 66.5% n-propanol.

Polyacrylamide Gel Electrophoresis

Samples of interferon ($1.5 \times 10^5$ Units) were incubated in NaDodSO$_4$ and 2-mercaptoethanol and then applied to a slab gel. After electrophoresis peaks $\alpha_1$, $\alpha_2$, $\beta_1$, $\beta_2$, $\beta_3$, $\gamma_1$, $\gamma_2$ and $\gamma_4$ gave single bands. Peaks $\gamma_3$ and $\gamma_5$ gave two bands. The apparent molecular weights were all in the range of 16,000 to 18,000 except $\beta_3$ and $\gamma_4$ which gave a 21,000 band.

TABLE 4

| Peak | $M_r$ | Spec. Act. on MDBK (Bovine cells, units/mg) | Spec. Act. on AG1732 (Human cells, units/mg) | Growth-inhibiting Activity** |
|---|---|---|---|---|
| | $\pm 1000$ | $\pm 25\%$ | $\pm 50\%$ | |
| $\alpha_1$ | 16,500 | $2.6 \times 10^8$ | $2.6 \times 10^8$ | + |
| $\alpha_2$ | 16,200 | $4 \times 10^8$ | $3 \times 10^8$ | + |
| $\beta_2$ | 16,500 | $4 \times 10^8$ | $2 \times 10^8$ | + |
| $\beta_3$* | 21,000 | $4 \times 10^8$ | $3 \times 10^8$ | + |
| $\gamma_1$ | 17,700 | $2.6 \times 10^8$ | $2 \times 10^8$ | + |
| $\gamma_2$ | 17,700 | $4 \times 10^8$ | $1.5 \times 10^8$ | + |
| $\gamma_3$* | 17,200 | $3.5 \times 10^8$ | $1.5 \times 10^7$ | + |
| $\gamma_4$ | 21,000 | $3.5 \times 10^8$ | $4 \times 10^8$ | + |
| $\gamma_5$* | 16,500 | $0.9 \times 10^8$ | $2 \times 10^6$ | + |

*2 bands on NaDodSO$_4$ polyacrylamide gel electrophoresis; MW of major band given
**Procedure of Stewart et al., Nature 262,300 (1976).

In subsequent preparations starting with cells from other CML patients it was possible to isolate species $\beta_1$ as a single peak eluting at 32% n-propanol from the Licrosorb RP-8 column. The $\beta_1$ was homogeneous and exhibited a specific activity of $1.7 \times 10^8$ on MDBK cells and $7.2 \times 10^8$ on human AG 1732 cells.

Additionally, when high titer starting preparations are employed in the purification procedure, the $\beta_3$ species is obtained in homogeneous form as a single peak eluting at 32% n-propanol from the Licrosorb RP-8 column. This material had a molecular weight of about 24,000 on polyacrylamide gel electrophoresis and exhibited a specific activity of $3.6 \times 10^8$ on MDBK (bovine) cells and $7.6 \times 10^8$ on human AG 1732 cells.

Amino Acid Analysis

Amino acid analysis of the purified human leukocyte interferons was performed with the fluorescamine amino acid analyzer on 0.5–1 μg samples of interferon. Hydrolysis was performed in 6N HCl under reducing conditions (0.1% thioglycolic acid). Amino acid analyses are summarized in Table 5.

TABLE 5

| AMINO ACID ANALYSES OF HUMAN LEUKOCYTE INTERFERONS | | | | | | | | | | | |
|---|---|---|---|---|---|---|---|---|---|---|---|
| Type | $\alpha_1$ | $\alpha_2$ | $\beta_1$ | $\beta_2$ | $\beta_3$* | $\beta_3$** | $\gamma_1$ | $\gamma_2$ | $\gamma_3$* | $\gamma_4$ | $\gamma_5$* |
| $M_r$ | 16,500 | 16,200 | 16,000 | 16,500 | 21,000 | 24,000 | 17,700 | 17,700 | 17,200 | 21,000 | 16,500 |
| Residues | 142 | 139 | 139 | 142 | 181 | 207 | 153 | 153 | 148 | 180 | 142 |
| Asx | 13.8 | 11.7 | 11.3 | 11.5 | 18.2 | 18.7 | 13.1 | 13.3 | 15.0 | 17.9 | 13.8 |
| Thr | 7.7 | 8.3 | 8.7 | 9.0 | 9.9 | 8.3 | 8.4 | 9.6 | 8.6 | 7.3 | 7.6 |
| Ser | 9.2 | 10.0 | 10.3 | 10.0 | 14.5 | 16.9 | 10.2 | 7.8 | 10.1 | 13.5 | 9.0 |
| Glx | 20.3 | 20.5 | 20.6 | 21.9 | 28.5 | 35.0 | 23.9 | 25.0 | 22.8 | 27.0 | 20.8 |
| Pro | 6.1 | 4.9 | 5.2 | 5.0 | 5.9 | 6.5 | 4.5 | 4.8 | 4.8 | 6.5 | 4.2 |
| Gly | 5.1 | 4.5 | 4.9 | 5.0 | 3.6 | 3.5 | 5.7 | 5.0 | 3.2 | 4.8 | 4.0 |
| Ala | 8.4 | 8.3 | 7.2 | 7.9 | 11.5 | 11.5 | 8.7 | 8.1 | 9.3 | 10.4 | 9.3 |
| Val | 7.4 | 6.2 | 6.0 | 6.7 | 7.5 | 8.3 | 7.3 | 7.0 | 5.5 | 7.9 | 5.1 |
| Met | 3.7 | 3.8 | 4.8 | 4.4 | 6.0 | 6.8 | 4.3 | 3.9 | 5.6 | 4.9 | 4.7 |
| ILeu | 7.4 | 7.0 | 6.4 | 7.4 | 9.5 | 11.6 | 7.9 | 8.0 | 6.8 | 9.7 | 6.6 |
| Leu | 18.0 | 18.0 | 18.1 | 18.9 | 24.4 | 26.0 | 20.3 | 20.1 | 20.5 | 24.1 | 19.6 |
| Tyr | 4.0 | 4.4 | 4.4 | 4.6 | 5.0 | 6.7 | 4.8 | 4.8 | 3.7 | 5.0 | 3.6 |
| Phe | 6.9 | 8.0 | 8.6 | 8.7 | 9.9 | 12.0 | 8.6 | 9.0 | 7.2 | 9.1 | 6.4 |
| His | 3.0 | 2.8 | 2.8 | 3.0 | 3.8 | 4.3 | 3.7 | 3.3 | 2.9 | 3.8 | 2.8 |
| Lys | 10.5 | 9.0 | 8.7 | 8.5 | 9.3 | 13.2 | 10.1 | 10.0 | 7.6 | 12.3 | 12.0 |
| Arg | 6.2 | 7.1 | 7.9 | 8.0 | 10.8 | 12.1 | 8.0 | 8.5 | 10.1 | 8.5 | 9.0 |
| Cys | 3.9 | 4.0 | 3.0 | 1.8 | 2.3 | — | 3.3 | 2.9 | 3.1 | 4.1 | 2.3 |

Accuracy ± 1.5 residues
*Composition of mixture of both bands
**homogeneous form Cleavage with trypsin and HPLC of the Fragments The various species of purified human leukocyte interferon (300 pmol, 6 μg) were dissolved in aqueous sodium bicarbonate (50 mM, pH 8.5 50 μl). TPCK trypsin (Worthington, 0.1 μg in 2 μl of HCl, pH 3) was added and the mixture was incubated 14 hr at 37° C. Acetic acid (5 μl) was added and the mixture was applied to a Licrosorb RP-8 column (10μ particle size, 4.6×250 mm). The column was eluted at 0.5 ml/min using a 1 hr linear gradient from 0 to 40% v/v n-propanol in 0.1M formic acid—0.03M pyridine buffer (pH 3). The peptides were detected by a fluorescamine monitoring system. The results are set forth in Table 6 and are expressed in % n-propanol and in relative size of the peaks (S-small, M-medium, L-large).

TABLE 6
TRYPTIC PEPTIDES OF INTERFERONS

Results of runs with eight individual species of human leukocyte interferon are summarized below in Table 7.

TABLE 7
Summary of Tryptic Peptide Maps of Human Leukocyte Interferon

| Peptide | $\alpha_1$ | $\alpha_2$ | $\beta_1$ | $\beta_2$ | $\beta_3$ | $\gamma_1$ | $\gamma_2$ | $\gamma_3$ | Correlation with Table 6 |
|---|---|---|---|---|---|---|---|---|---|
| T 1** | <u>37.5(L)</u> | <u>37.5(L)</u> | <u>36.5(L)</u> | 33(L) | 22.5(M) 23.5(M) 35.5(L) | 35.5(L) | 35(L) | 33.5(L) | 3L |
| T 2** | <u>39(L)</u> | <u>39(L)</u> | <u>38(L)</u> | 36(L) | 37.5(L) | 37(L) | 36.5(L) | | 4L |
| T 3** | 67.5(L) | <u>68.5(L)</u> | <u>68.5(L)</u> | 67.5(L) | 65(S) | 67.5(S) | 67(S) | 64(S) | 11.5M |
| T 4 | 78(S) | 79(S) | 79.5(S) | 78.5(S) | 77(M) 79.5(S) | 78(S) | 77(S) | 78.5(S) 82(M) | 12.5(S) |
| T 5** | 84.5(L) | <u>85.5(L)</u> | <u>85.5(L)</u> | 85(L) | 85.5(L) | 84(L) | 83(L) | 84.5(L) | 14.5M |
| T 6 | 90(S) | 90(S) | 91.5(S) | 90.5(S) | 90.5(S) | 89.5(S) | 89.5(S) | | |
| T 7 | 94(S) | 94.5(S) | 95(S) | 94(S) | | 93(S) | 92(S) | 92(S) | 16S |
| T 8 | 95(S) | 95.5(S) | 96(S) | 95(S) | | 94(S) | 93(S) | 93.5(S) 98.5(S) | |
| T 9* | 105.5(L) | <u>106.5(L)</u> | <u>106.5(L)</u> | 105.5(L) | 105.5(L) | 102.5(M) 105.5(L) | 100.5(M) 104(L) | 104(L) | 18M |
| T 10* | 122.5(M) | 123(M) | <u>122.5(M)</u> | 122(M) | 111(L) 165(L) | 122(M) | 120(M) | 107(L) | 19.5M |
| T 11* | 170(S) | 169.5(S) | 171(S) | 169.5(S) | | 172(S) 166(S) | 172.5(S) | 172.5(M) | 27M |
| T 12* | 177(L) | 176.5(L) | <u>176.5(M)</u> | 177(L) | | 177(S) 179.5(L) | 184(M) | 177(S) | 29M |

*Amino acid composition determined ———
**Sequence + Amino acid compositions determined ═══
Legends for the Table of Tryptic Peptides Maps
(S) small response with fluram
(M) medium response with fluram
(L) large response with fluram
The numbers represent elution times in minutes

| Type | Elution Positions (% of n-propanol) |
|---|---|
| $\alpha_1$ | 3L, 4L, 4.2M, 11.5M, 12.5S, 14.5M, 16S, 18M, 20S, 21S, 22.5S, 29M |
| $\alpha_2$ | 3L, 4L, 4.2M, 11.5M, 12.5S, 14.5M, 16S, 18M, 27S, 29M |
| $\beta_2$ | 3L, 4L, 4.2M, 11.5M, 12.5S, 14.5M, 16S, 17.5S, 18M, 29M |
| $\beta_3$ | 3L, 4L, 4.2M, 4.5S, 10M, 12.5S, 14S, 14.5M, 16S, 18L, 19.5M, 27M, 32M |
| $\gamma_1$ | 3L, 4L, 4.2M, 4.5S, 5S, 6.5S, 11.5S, 12.5S, 14.5M, 16S, 17.5M, 18M, 29M |
| $\gamma_2$ | 3L, 4L, 4.2M, 4.5S, 5S, 11.5S, 12.5S, 14.5S, 16S, 18L, 29M |
| $\gamma_3$ | 3M, 4M, 4.2M, 11.5M, 12.5S, 13.5S, 14.5M, 16S, 18L, 20S, 32M |
| $\gamma_5$ | 3L, 4L, 4.2M, 4.5M, 7S, 7.5S, 10S, 11.5L, 12.5S, 14S, 14.5M, 16S, 18L, 24.5S, 25.5S, 32S |

Sequence of Tryptic Digests

A sample of a homogeneous species of interferon (200 p moles, 4 μg) was lyophilized and dissolved in sodium bicarbonate solution (0.1M, 50 μl). TPCK Trypsin (Worthington) was dissolved in dilute HCl pH 4 (1 μg in 10 μl) and 2 μl (0.2 μg) of this solution were added to the interferon solution. The mixture was incubated 14 hours at 37° C. β-Mercaptoethanol (5 μl) was then added and after 60 min at 25° C. a pyridine-formate buffer (1M, pH 4, 45 μl) was added and the mixture was kept at −20° C. until it was analysed. Each sample was applied to an Ultrosphere-octyl 4.6×250 mm (5μ particle size) HPLC column (Altex Scientific) pre-equilibrated with 0.1M formic acid 0.03M pyridine buffer (pH-3). The column was eluted by a linear gradient of n-propanol from 0 to 40% (v/v) in the pyridine formate buffer for 3 hr. at a flow rate of 0.75 ml/min. The peptides were detected by a fluorescamine monitoring system. The chart speed of the recorder was 1 mm/min.

The full or partial sequence of peptides T1, T2, T3, T5 and T9 taken from multiple runs using peptides from one or more species as indicated in Table 7 was determined by Edman degradation procedures described by Tarr, Methods In Enzymology, Vol. XLVII, pp. 335–357 (1977). The amino acid analysis for all the tryptic peptides was run as described previously in this Example. The results of such sequence and amino acid analysis are summarized in Tables 8 and 9 below:

TABLE 8
Sequence Data on Various Tryptic Peptides of Human Leukocyte Interferon

| Residue from N Terminus | T1 | T1 minor comp. | T2 | T3 | T5 | T9 |
|---|---|---|---|---|---|---|
| 1 | Ala | Tyr | Lys | Glx | Ile | Thr |
| 2 | Glu | Phe | Tyr | Asx | Thr | Leu |
| 3 | Ile | Gln | Phe | Ser | Leu | Met |
| 4 | Met | Arg | Gln | Ile | Tyr | Leu |
| 5 | Arg | | Arg | Leu | Leu | — |
| 6 | | | | Ala | Lys | — |
| 7 | | | | Val | | — |
| 8 | | | | Arg | | — |
| 9 | | | | | | Arg |

TABLE 9
Amino Acid Compositions of Various Tryptic Peptides of Human Leukocyte Interferon

| Peptide | Residue | | | | | |
|---|---|---|---|---|---|---|
| T9 | Thr | Glx | Ala | Met-2 | Leu-3 | Arg |
| T10 | Ser-2 | Ile | Leu-2 | Phe | Lys | Cys |
| T11 | Asx-2 Ala | Thr-2 Val | Ser Leu-3 | Glx-3 Tyr | Pro Lys | Gly |

TABLE 9-continued

Amino Acid Compositions of Various Tryptic Peptides of Human Leukocyte Interferon

| Peptide | Residue | | | | | |
|---|---|---|---|---|---|---|
| T12 | Asx | Thr-2 | Ser | Glx-3 | Pro | Ala |
| | Val | Met | Ile-2 | Leu-2 | Phe-2 | His |
| | Lys | | | | | |

Sequence of T1 gave an additional minor component which appears to be a fragment of the T2 peptide.

Amino Sugar Analysis

The purified human-leukocyte interferon species were subjected to amino sugar analysis capable of identifying amino sugars at the 50–100 p mol level. In all instances glucoseamine and galactose/mannose amine was below 1 residue per molecule. In most cases by a number of small peptides which eluted near the amino-sugars interfered with the analysis. It is thus possible that even the peaks assigned as amino sugars are at least in part of a peptide nature.

NH$_2$-terminus Analysis

Aminopeptidase M digestion was used to investigate the NH$_2$ terminal of the human leukocyte interferon species. This enzyme cleaves peptide bonds sequentially from the NH$_2$-terminus providing that the $\alpha$ NH$_2$ group of the terminal amino acid is unblocked. Theoretically, each individual amino acid will be liberated quantitatively if the reaction is allowed to go to completion. In cases where the $\alpha$ amino group of the terminal amino acid is blocked, no amino acids will be released from the protein.

Each species of human leukocyte interferon (two hundred picomoles) was dried under vacuum and suspended in 15 $\mu$l of 0.1M sodium phosphate, pH 7.0, containing 75 $\mu$g/ml of aminopeptidase M (Pierce Chemical Co.). The samples were sealed in 25 $\mu$l capillary tubes and incubated at 37° C. for 18 hours. The resulting solution was diluted with 125 $\mu$l of 0.2N sodium citrate buffer pH 2.2 and subjected to amino acid analysis on a fluorescamine analyzer. The yield of free serine, the NH$_2$-terminal amino acid, was calculated and used to quantitate the percentage of blocked NH$_2$ termini for each species.

The results of these experiments are summarized below in Table 10.

TABLE 10

RELEASE OF NH$_2$—TERMINAL AMINO ACIDS BY AMINOPEPTIDASE

| Interferon Species | Picomoles of Serine Released | Serine Released Interferon Molecule |
|---|---|---|
| $\alpha$1 | 150 | 0.75 |
| $\alpha$2 | 28 | 0.14 |
| $\beta$1 | 39 | 0.19 |
| $\beta$2 | 149 | 0.74 |
| $\beta$3 | 112 | 0.56 |
| $\gamma$1 | 56 | 0.28 |
| $\gamma$2 | 14 | 0.07 |
| $\gamma$3 | 84 | 0.42 |

Serine was the most abundant amino acid in each case. Smaller amounts of aspartic acid and leucine were also released, corroborating the NH$_2$-terminal amino acid sequence. Up to 30 picomoles of serine were found in blanks, and this value was substracted from the actual values. Picomoles of interferon were calculated on the basis of 3 histidines per molecule.

EXAMPLE 3

Parenteral Dosage Form With Homogeneous Human Leukocyte Interferon (a) A total of 3 mg of homogeneous human leukocyte interferon having a specific activity of $2 \times 10^8$ units/mg is dissolved in 25 ml of 5% normal serum albumin (human)-U.S.P. the solution passed through a bacteriological filter and the filtered solution aseptically subdivided into 100 vials. Each vial contains $6 \times 10^6$ units of the pure interferon suitable for parenteral administration. The vials are preferably stored in the cold ($-20°$ C.) prior to use.

(b) An aqueous solution containing 1.5 mg of pooled homogeneous human leukocyte interferon species $\alpha_1$, $\alpha_2$, $\beta_2$, $\gamma_1$ and $\gamma_2$ each present proportionally to their approximate natural abundance, the pooled mixture having a specific activity of about $2 \times 10^8$ units/mg, and 100 mg of normal serum alubmin (human) U.S.P. is passed through a bacteriological filter and the filtered solution aseptically subdivided into 100 vials. Each vial will contain about $3 \times 10^6$ units of the pure pooled interferons and 1 mg of the serum albumin. The vials containing interferon suitable for parenteral administration are preferably stored in the cold ($-20°$ C.) prior to use.

EXAMPLE 4

In analogy to the procedures of Example 1, pooled bovine leukocytes are prepared, induced to produce bovine interferon and the resulting bovine interferon is purified to homogeneity in the form of distinct species of homogeneous proteins.

EXAMPLE 5

In analogy to the procedures of Example 1, pooled porcine leukocytes are prepared, induced to produce porcine interferon and the resulting porcine interferon is purified to homogeneity in the form of distinct species of homogeneous proteins.

EXAMPLE 6

In analogy to the procedures of Example 1, pooled ovine leukocytes are prepared, induced to produce ovine interferon and the resulting ovine interferon is purified to homogeneity in the form of distinct species of homogeneous proteins.

EXAMPLE 7

In analogy to the procedures of Example 1, pooled equinine leukocytes are prepared, induced to produce equinine interferon and the resulting equinine interferon is purified to homogeneity in the form of distinct species of homogeneous proteins.

EXAMPLE 8

In analogy to the procedures of Example 1, pooled canine leukocytes are prepared, induced to produce canine interferon and the resulting canine interferon is purified to homogeneity in the form of distinct species of homogeneous proteins.

EXAMPLE 9

In analogy to the procedures of Example 1, pooled feline leukocytes are prepared, induced a produce feline interferon and the resulting feline interferon is purified to homogeneity in the form of distinct species of homogeneous proteins.

EXAMPLE 10

In analogy of the procedures of Example 1, pooled primate leukocytes are prepared, induced to produce primate interferon and the resulting primate interferon is purified to homogeneity in the form of distinct species of homogeneous proteins.

EXAMPLE 11

1.5 liter of crude fibroblast interferon (20,000 units/ml; 1 mg protein/ml) were mixed with 0.27 volumes of saturated NaCl-solution (~6.3M) by end over end rotation of the bottle. This solution was pumped through Blue Dextran Sepharose (35 ml) packed in a 50 ml polypropylene syringe equipped with a porous polyethylene disk at the bottom (100 ml/hr flow rate). The charged resin was washed in sequence with 200 ml of 1M NaCl containing 0.05M sodium phosphate buffer (pH 7.2); 500 ml of 1M NaCl containing 0.05M sodium phosphate (pH 7.2) and 75 ml of ethylene glycol and finally eluted with 500 ml of 1M NaCl containing 0.05M sodium phosphate (pH 7.2) and 250 ml ethylene glycol. About 90% of the interferon came down in a peak with the front of the 50% ethylene glycol. The specific activity in the peak maximum, where more than 50% of the total interferon eluted, was $1 \times 10^7$ units/mg.

Preparation of the Blue Dextran Resin

Fifty grams of packed Sepharose 4B were washed with 1 liter of water and resuspended in 50 ml of distilled water. Fifteen grams of finely divided cyanogen bromide were added to the slowly stirred solution and the pH was immediately adjusted to and maintained at 11±0.2 by dropwise addition of 10N NaOH. Temperature was maintained at 20±5° C. by small additions of crushed ice. When the reaction had subsided (15-20 min) about 1 vol. of ice-water was added, the suspension transferred into a Buchner funnel and further washed with 5 volumes of 0.01N HCl.

The activated resin was immediately suspended in 50 ml of 0.4M sodium carbonate buffer (pH 9.5) containing 1.00 g of dissolved Blue Dextan and rotated overnight at 4° C. in a round bottom flask. The resin was then washed with 10 volumes of 1M NaCl, 2 vol. of 50% ethylene glycol containing 1M NaCl and 0.05M sodium phosphate (pH 7.2), left overnight in the 50% ethylene glycol, washed with 1 vol. 80% ethylene glycol and 5 vol. Gibco #11 MEM culture medium containing 5% fetal calf serum and left in this medium overnight at 50° C. After further washings with 80% ethylene glycol containing 1M NaCl (3 volumes) and then with culture medium containing 5% fetal calf serum (2 volumes) the resin is then slurried in culture medium (MEM) containing 5% fetal calf serum and packed in a column for use.

By measurement of the absorption at 280 nm of the first wash it was estimated that 0.7-0.8 g Blue Dextran/50 ml resin had been coupled.

EXAMPLE 12

Concanavalin A Affinity Chromatography 50 ml of Concanavalin A-Sepharose which is equilibrated with PBS buffer containing 0.1M alpha-methylmannoside was packed in a 50 ml polypropylene syringe equipped with a poylethylene disk frit. It was loaded at 180 ml/hr flow rate with 1.25 liters of crude interferon (20,000,000 units) having a specific activity of $2 \times 10^4$ units/mg. The charged column was washed with 150 ml of PBS buffer and 600 ml of PBS buffer containing 0.1M of alpha-methylmannoside. Interferon was finally eluted with the above buffer containing 50% ethylene glycol. Yield of the procedure 9% (3 million units) with a specific activity of about $1 \times 10^7$ units/mg.

EXAMPLE 13

HPLC with Con A Eluent

A total of 120 ml of eluent from the Con A column (2,500,000 units; approx. $2-4 \times 10^7$ units/mg) was applied directly to a Chromegabond $10\mu$ (E. S. Industries) cyclohexyl-column (4.6×300 mm) which had been equilibrated with pyridine formic acid (8%/8%; v/v) containing 20% isopropanol (Buffer A) at flow rates in the range 0.4-0.8 ml/min keeping the maximal back-pressure below 4500 psi. The system used for the high performance liquid chromatography procedures was essentially that described by Bohlen et al., supra.

A 4 hour gradient from equilibrating buffer A to final buffer B (pyridine 8%-formic acid 8% containing 25% isopropanol+20% n-butanol) was run at 0.4 ml/min (0-25% B, 32 min; 25-60% B, 225 min; 60-100% B, 63 min). Fractions of 2.0 ml were collected. A pool comprising fractions 26-29 (2,000,000 units) in the center of the activity peak was taken and diluted with pyridine-formic acid (8 ml+4 ml pyridine-formic acid). This solution was applied through the pump to a Chromegabond $10\mu$ octyl column (4.6×300 mm). The elution conditions were the same as for the cyclohexyl column above. The specific activity in the center of the activity peak was approximately $4 \times 10^8$ units/mg with a total yield of purified human fibroblast interferon of 1,000,000 units.

It should be noted that the elution position of the interferon on both the cyclohexyl and octyl columns is very close to the main central peak when interferon purified on a Con A is subject to HPLC on either column. If the first HPLC step is carried out on an octyl column the interferon elutes right before the main central peak, while it elutes immediately after that peak under the same chromatography conditions on the cyclohexyl column.

EXAMPLE 14

HPLC With Blue Dextran Sepharose Eluent (A) A total of 125 ml of pooled interferon eluted from the Blue Dextran Sepharose column (30,000,000 units; $1 \times 10^7$ units/mg were pumped on a 4.6×300 mm. Chromegabond $10\mu$ octyl column which had been pre-equilibrated with 1M NaCl containing 50% ethylene glycol. Immediately after sample application A-buffer (pyridine-formic acid, 8%/8%, plus 20% isopropanol and 3.3% n-butanol, v/v) was pumped on the column. A gradient to B-buffer (pyridine-formic acid 8%/8% plus 25% isopropanol and 20% n-butanol) with the following program was run at a flow rate of 0.45 ml/min.: 0-25% B-30 min.; 25-55% B, 190 min; 55-100% B, 20 min, then 100% B was run for another 60 min. Interferon activity was found to coincide essentially with a single protein peak found in tubes 18-23 (each tube contained 1.5 ml of eluent.)

(B) When approximately one-fourth the load in run (A) above was applied to the same column and the elution conditions used for the cyclohexyl column in Example 3 were employed interferon activity was found to coincide with a protein peak found in tubes 24-26.

(C) Using the same loading, gradient program and linear flow rate as in (A) and the A and B buffers used in (B) with a 9.6×500 mm Chromegabond octyl column which thus provided about 1/9th the loading per column volume, and resulted in a better separation quality.

(D) The material exhibiting the highest specific activity ($4 \times 10^8$ units/mg) from run (A) above was rechromatographed on a MN cyanopropyl column using 8% pyridine/8% formic acid 0–40% n-propanol (v/v) with a 1 hour gradient at 0.3 ml/minute to provide a symmetrical main peak.

EXAMPLE 15

NaDodSO$_4$: Polyacrylamide Gel Electrophoresis of Purified Human Fibroblast Interferon Samples of purified human fibroblast interferon obtained from Example 3 were run on 12.5 or 15% (NaDodSO$_4$) polyacrylamide gels in Tris/glycine buffer with 1 μg of protein for the run. After electrophoresis, a single band was obtained upon staining with Coomassie blue. The same sample material was run in a parallel gel and the gel sliced for antiviral assay. The maximum of the antiviral activity coincided with the center of the stained band. A molecular weight of about 20,500 was determined using bovine serum albumin (BSA), chymotrypsin, cytochrome C and ribonuclease as standards. The relative mobility of the human fibroblast band was the same whether mercaptoethanol was in the sample or not.

Samples from procedures (A), (B) and (C) of Example 4 showed as major band the 20,500 MW band, which when gels were sliced and assayed coincided with the center of the activity peak. The second strongest band (10,500 MW/20–50% of total material as estimated from the staining intensity) varied from sample to sample and had no antiviral activity. If samples were not treated with mercaptoethanol, a 40,000 MW band could be observed, which had borderline activity. Amino acid analysis of the 20,000 and 40,000 bands were indistinguishable while the analysis of the 10,000 band was very significantly different.

Electrophoresis of a sample from procedure (D) of Example 4 provided a single band which had a molecular weight of about 20,500 and a specific activity of $4 \times 10^8$ units/mg. An amino acid analysis of this homogeneous peptide carried out on a 24 hour hydrolysate in 6N HCl gave the following values:

Asx: 15.4±0.2
Thr*: 7.8±0.3
Ser*: 7.7±0.2
Glx: 24.1±0.4
Pro: 2.8±0.4
Gly: 4.9±0.3
Ala: 11.8±0.4
Cys: n.d.
Val: 6.9±0.1
Met: 2.8±0.4
Ile: 8.7±0.1
Leu: 25.0**
Tyr: 9.6±0.2
Phe: 7.3±0.1
His: 4.5±0.1
Lys: 11.6±0.4
Arg: 8.8±0.4
Trp: n.d.

*These values are uncorrected for losses during hydrolysis.
**Arbitrary value
n.d.=not determined

EXAMPLE 16

Parenteral Dosage Form with Homogeneous Human Fibroblast Interferon

A total of 1.5 mg of homogeneous human fibroblast interferon having a specific activity of $4 \times 10^8$ units/mg is dissolved in 25 ml of 5% normal serum albumin (human) USP, the solution passed through a bacteriological filter and the filtered solution aseptically subdivided into 100 vials. Each vial contains $6 \times 10^6$ units of the pure interferon suitable for parenteral administration. The vials are preferably stored in the cold ($-20°$ C.) prior to use.

EXAMPLE 17

Isolation of Pro-opiocortin

One lyophilized camel pituitary (200 mg) was homogenized in 4 ml of a solution containing 1M acetic acid, 20 mM hydrochloric acid, 0.1% (vol/vol) 2-mercaptoethanol, pentachlorophenol at 1 μg/ml, phenylmethylsulfonyl fluoride at 10 μg/ml, and peptstatin at 10 μg/ml. The homogenate was centrifuged at 26,000×g for 30 min. The precipitate was extracted with an additional 4 ml of the same acid solution and again centrifuged. The combined supernatant solutions (7 ml) were clarified by centrifugation at 200,000×g for 1 hr, concentrated to 4 ml under reduced pressure, and fractionated on a Sephadex G-100 (superfine) column (1.5×90 cm) equilibrated with 1M acetic acid/20 mM HCl/0.01% (vol/vol) thiodiglycol. Aliquots of each fraction were lyophilized and digested with 40 μg of trypsin treated with tosylphenylalanyl chloromethyl ketone (TPCK) in 200 μl of 50 mM Tris HCl buffer (pH 8.5) at 37° C. for 16 hr. Opioid activity was measured with a radioreceptor binding assay. The highest molecular weight species yielding opioid activity after trypsin digestion was evaporated under vacuum to reduce the volume to 4 ml. It was then applied to a Sephadex G-75 (superfine) column (1.5×90 cm) equilibrated with the same buffer as the Sephadex G-100 column and fractions were assayed as described above. The pro-opiocortin-containing fractions from the Sephadex G-75 column were subjected to high-performance liquid chromatography (HPLC) on a reverse-phase column (EM Lichrosorb RP-8, 4.6×250 mm, Scientific Products, Edison, N.J.). The column was eluted with a 2-hr linear gradient of 0–40% (vol/vol) 1-propanol in 0.5M formic acid/0.14M pyridine (pH 3.0) at a flow rate of 30 ml/hr. The column effluent was monitored by an automated fluoroescence-detection system. Aliquots from fractions were assayed for opioid activity as above. The fraction showing the highest specific activity was rechromatographed on the same reverse-phase column, using a 4-hr gradient of 1-propanol at a flow rate of 15 ml/hr.

EXAMPLE 18

The purification of human leukocyte interferon from chronic myelogenous leukemia (CML) cells has been described previously. Human leukocyte interferon species $\alpha_1$ and $\beta_2$ were sequenced with a modified Beckman spinning cup sequenator. Peptide fragments of $\alpha_1$, $\alpha_2$, and $\beta_1$ species were produced by digestion with trypsin and purified by high preformance liquid chromatography (HPLC). Tryptic peptides were sequenced manually by the Edman reaction and the phenylthiohydantoin derivatives of the amino acids were identified by HPLC.

Automatic Edman degradations were performed in a modified Beckman 890C sequenator on 1.7 nmoles of species $\alpha_1$ of human leukocyte interferon. The modifications which are similar to those described by Wittman-Liebold and Hunkapiller and Hood include an improved vacuum system, improved reagent and solvent delivery system, extensive solvent and reagent purification, and a device which automatically converts anilinothiazolinone to phenylthiohydatoin (PTH) derivatives of amino acids. Proteins are retained in the spinning cup with 6 mg of polybrene which, together with 100 nmoles of glycylglycine, has been subjected to 7 precycles of Edman degradation. PTH-amino acids were analyzed by high performance liquid chromatography on DuPont Zorbax ODS or CN columns at 254 nm and 313 nm on a Waters Associates chromatograph. Peak assignments, except for serine, were made by chromatography on a DuPont Zorbax ODS column. PTH-serine was identified as the "dehydro" derivative on a CN column. Peaks were integrated and gradient elution was controlled by a Spectra Physics SP4000 integration system. All PTH derivatives were detected at 254 nm, except for those of serine and threonine which were detected at 313 nm.

The composition of the first two tryptic peptides of species $\alpha_1$, $\alpha_2$, and $\beta_1$ of human leukocyte interferon are shown in Table 11.

TABLE 11

| Peptide | Composition |
|---|---|
| 1 | ASX(2),THR,SER(2),GLX,GLY,LEU(2),HIS, ARG(2),PRO |
| 2 | THR,GLX,ALA,MET(2),LEU(3),ARG |
| 2 | THR—LEU—MET—LEU—(LEU,GLX,ALA, MET)—ARG |

The amino terminal peptide had been identified before sequence data were available by analysis of a tryptic digest of interferon ($\alpha_2$) which was blocked at the amino terminus and, therefore, would not react with fluorescamine. Peptide 2 was sequenced manually and was identified as the penultimate tryptic peptide by comparison with the sequence determined by the automatic sequenator. Manual Edman degradation provided the sequence of the first four amino acids as well as the terminal arginine.

Table 12 shows the NH$_2$-terminal sequence based on analysis of 1.7 nmoles of human leukocyte interferon species $\alpha_1$. Based on the yield of leucine at cycle 3 (540 nmoles) and a repetitive yield of 92% (calculated from the leucines at cycles 3 and 9), the yield of the NH$_2$-terminal serine was calculated to be 41%. The high yield of the NH$_2$ terminus and the determination of a single sequence from residenes 1 through 21 confirms that this protein is a pure single species. The assignments of asn$^{11}$, arg$^{12}$, thr$^{14}$, and leu$^{18}$ were made with less confidence, since their yields were somewhat lower than expected. However, it should be noted that no other PTH amino acid was seen for these cycles. Although the identification of thr$^{14}$ is tentative from the data by automatic sequencing, it is clear that alanine (reported for this position for lymphoblastoid interferon by Zoon, et al., Science 207, 528 (1980) is not found at this position in human leukocyte interferon species $\alpha_1$. It is evident from the manual sequence Table 11 that the NH$_2$-terminal threonine of peptide 2 must correspond to position 14. Peptide 2 was the only one whose composition and sequence matched positions 14–22. Furthermore, although arg$^{22}$ was not identified on the automatic sequenator, it was clearly identified as the COOH terminus of peptide 2. These results are consistent with our assignment of the first 22 NH$_2$-terminal amino acids as shown in Table 12.

TABLE 12

1
SER—ASP—LEU—PRO—GLN—THR—HIS—SER—LEU—

10    11
GLY—ASN—ARG—ARG—THR—LEU—MET—LEU—LEU—

20    21
ALA—GLN—MET—ARG—

The sequence reported is identical to the published results for human lymphoblastoid interferon by Zoon, et al. through position 20 with two exceptions. Threonine has been found instead of alanine at position 14, and methionine instead of isoleucine at position 16. It is possible that these results demonstrate that leukocyte interferon differs structurally from lymphoblastoid interferon. This may result from the expression of different structural genes or possibly mutations that have become stabilized in the lymphoblastoid cells during long-term culture. The positions of 9 amino acids (positions 2-6, 9-11, and 15) are identical to those in mouse interferon, see Faira, et al., Science 207, 528 (1980).

It is noteworthy that 8 species of human leukocyte interferon have been purified to homogeneity. In general, these appear to have similar tryptic peptide maps. However, some structural differences between these species are likely. Some differences may relate to extent of glycosylation and other modifications. However, it appears that one or more internal peptides may differ in sequence suggesting that two or more different alleles are expressed. Furthermore, isolation of human leukocyte interferon from lymphoblasts and from a granulocytic cell line appear to have distinct structures. Accordingly, human leukocyte interferon represents a class of molecules exhibiting distinct but closely related primary amino acid sequences. Recombinant-DNA plasmids containing leukocyte interferon sequences appear to represent distinct but homologous sequences. Of further note is that monoclonal antibodies to human leukocyte interferon interact differently with several of the individual purified leukocyte interferon species. All these observations lead us to postulate the existence of a mechanism that generates diversity in the primary structure of human leukocyte interferon.

RESULTS

The first chromatographic step for the purification of camel pro-opiocortin was on Sephadex G-100. The high molecular weight region contained two peaks that showed opioid activity after digestion with trypsin, corresponding in molecular weights to pro-opiocortin (ca. 30,000) and $\beta$-lipotropin (10,000). Rechromatography on Sephadex G-75 was used to complete the separation of pro-opiocortin from $\beta$-lipotropin and other proteins of similar size. Reverse-phase chromatography resolved several major protein peaks, one of which corresponded with the opioid activity. The fraction having the highest specific activity (fraction 25) was rechromatographed under similar conditions, except for the collection of smaller fractions (0.75 ml) and the use of a lower flow rate (15 ml/hr). A single symmetrical peak was obtained. The fraction with the highest specific activity (fraction 50) was found to be homogeneous by polyacrylamide gel electrophoresis in NaDodSO$_4$. About 5 nmol of pure pro-opiocortin was isolated from the extract of one camel pituitary by this procedure. This represented a 77-fold purification from the initial acid extract with a 15% overall yield. Five other camel pituitaries were carried through the same procedure. Yields as high as 50% were obtained with these pituitaries by rechromatographing less pure fractions.

We claim:

1. Human leukocyte interferon as a homogenous protein species having a specific activity of from $0.9 \times 10^8 - 4 \times 10^8$ Units/mg. of protein when assayed on the MDBK bovine cell line and from $2 \times 10^6 - 7.6 \times 10^8$ Units/mg. of protein when assayed on the AG 1732 human cell line.

2. The homogeneous human interferon of claim 1 which is a human leukocyte interferon characterized by containing the following amino acid sequences:
   (I) ... Ala-Glu-Ile-Met-Arg ...
   (II) ... Tyr-Phe-Gln-Arg ...
   (III) ... Ile-Thr-Leu-Tyr-Leu-Lys ... , and
   (IV) ... Thr-Leu-Met-Leu-Leu-Ala-Gln-Met-Arg ...

3. Human leukocyte interferon as a mixture of human leukocyte interferon species according to claim 1.

4. A pharmaceutical preparation suitable for parenteral administration for treatment of viral and neoplastic disease states said preparation comprising a minor, effective amount of at least one human leukocyte interferon species according to claim 1 and a major amount of a conventional pharmaceutical parenteral carrier material.

5. A species of human leukocyte interferon designated $\alpha_1$ being a homogeneous protein characterized by the following:
   (a) an amino terminal sequence as follows: Ser-ASp-Leu-Pro-Gln-Thr-His-Ser-Leu-Gly-Asn-Arg-Arg-Thr-Leu-Met-Leu-Leu-Ala-Glu-Met-Arg- ...
   (b) a specific activity on MDBK (bovine cells) of about $2.6 \times 10^8$ Units/mg;
   (c) a specific activity on Ag 1732 (human line) cells of about $2.6 \times 10^8$ units/mg;
   (d) a molecular weight of about $16,500 \pm 1000$ by polyacrylamide gel electrophoresis
   (e) an amino sugar content of less than 1 residue per molecule;
   (f) positive growth inhibition activity;
   (g) eluted as a single peak at a concentration of 31% n-propanol (0-40% gradient) in a 1M pyridine—2M formic acid aqueous buffer from an octyl bonded silica matrix HPLC 4.6×250 mm column at room temperature and a flow rate of 0.2 ml/min;
   (h) an amino acid composition ($\pm 15\%$) as based on a molecular weight of 16,500 as contained in the following table:
   Asx: 13.8
   Thr: 7.7
   Ser: 9.2
   Glx: 20.3
   Pro: 6.1
   Gly: 5.1
   Ala: 8.4
   Val: 7.4
   Met: 3.7
   ILeu: 7.4
   Leu: 18.0
   Tyr: 4.0
   Phe: 6.9
   His: 3.0
   Lys: 10.5
   Arg: 6.2
   Cys: 3.9
   (i) providing peptide fragments upon treatment with trypsin, and fragments eluting as peaks at 3(L), 4(L), 4.2(M), 11.5(M), 12.5(S), 14.5(M), 16(S), 18(M), 20(S), 21(S), 22.5(S) and 29(M)% n-propanol when the reaction media is passed through an octyl bonded silica matrix 10$\mu$ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient; and
   (j) containing the following amino acid sequences:
   (I) ... Ala-Glu-Ile-Met-Arg ... ,
   (II) ... Lys-Tyr-Phe-Gln-Arg ... ,
   (III) ... Glx-Asx-Ser-Ile-Leu-Ala-Val-Arg ... ,
   (IV) ... Ile-Thr-Leu-Tyr-Leu-Lys ... ,
   (V) ... Thr-Leu-Met-Leu-Leu-Ala-Gln-Met-Arg ... ,
   (VI) ... (Ser-2, Ile, Leu-2, Phe, Lys, Cys) ... ,
   (VII) ... (Asx-2, Thr-2, Ser, Glx-3, Pro, Gly, Ala, Val, Leu-3, Tyr, Lys) ... ,
   (VIII) ... (Asx, Thr-2, Ser, Glx-3, Pro, Ala, Val, Met, Ile-2, Leu-2, Phe-2, His, Lys) ...

6. A species of human leukocyte interferon designated $\alpha_2$ being a homogeneous protein characterized by the following:
   (a) a blocked amino terminus;
   (b) a specific activity on MDBK (bovine cells) of about $4.0 \times 10^8$ units/mg;
   (c) a specific activity on Ag 1732 (human line) cells of about $3 \times 10^8$ units/mg;
   (d) a molecular weight of about $16,200 \pm 1000$ by polyacrylamide gel electrophoresis;
   (e) an amino sugar content of less than 1 residue per molecule;
   (f) positive growth inhibition activity;
   (g) eluted as a single peak at a concentration of 32% n-propanol (0-40% gradient) in a 1M pyridine—2M formic acid aqueous buffer from an octyl bonded silica matrix HPLC 4.6×250 mm column at room temperature and a flow rate of 0.2 ml/min;
   (h) resistant to deactivation by treatment with leucine aminopeptidase and aminopeptidase M;
   (i) an amino acid composition ($\pm 15\%$) as based on a molecular weight of 16,200 as contained in the following table:
   Asx: 11.7
   Thr: 8.3
   Ser: 10.0
   Glx: 20.5
   Pro: 4.9
   Gly: 4.5
   Ala: 8.3
   Val: 6.2
   Met: 3.8
   ILeu: 7.0
   Leu: 18.0
   Tyr: 4.4
   Phe: 8.0
   His: 2.8
   Lys: 9.0
   Arg: 7.1

Cys: 4.0
(j) providing peptide fragments upon treatment with trypsin said fragments eluted as peaks at 3(L), 4(L), 4.2(M), 11.5(M), 12.5(S), 14.5(M), 16(S), 18(M), 27(S) and 29(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient;
(k) eluted as a single peak at a concentration of 68% n-propanol (72.5-50% gradient) in 0.1M sodium acetate aqueous buffer from a glycerol bonded silica matrix HPLC 4.6×250 mm column at room temperature and a flow rate of 0.25 ml/min. and
(l) containing the following amino acid sequences:
  (I) ... Ala-Glu-Ile-Met-Arg ... ,
  (II) ... Lys-Tyr-Phe-Gln-Arg ... ,
  (III) ... Glx-Asx-Ser-Ile-Leu-Ala-Val-Arg ... ,
  (IV) ... Ile-Thr-Leu-Tyr-Leu-Lys ... ,
  (V) ... Thr-Leu-Met-Leu-Leu-Ala-Gln-Met-Arg . . . ,
  (VI) ... (Ser-2, Ile, Leu-2, Phe, Lys, Cys) ... ,
  (VII) ... (Asx-2, Thr-2, Ser, Glx-3, Pro, Gly, Ala, Val, Leu-3, Tyr, Lys) ... ,
  (VIII) ... (Asx, Thr-2, Ser, Glx-3, Pro, Ala, Val, Met, Ile-2, Leu-2, Phe-2, His, Lys) ... .

7. A species of human leukocyte interferon designated $\beta_1$ being a homogeneous protein characterized by the following:
(a) a blocked amino terminus;
(b) a specific activity on MDBK (bovine cells) of about $1.7 \times 10^8$ units/mg;
(c) a specific activity on Ag 1732 (human line) cells of about $2.2 \times 10^8$ units/mg;
(d) a molecular weight of about 16,000($\pm$1000) by polyacrylamide gel electrophoresis;
(e) an amino sugar content of less than 1 residue per molecule
(f) positive growth inhibition activity;
(g) eluted as a single peak at a concentration of 31% n-propanol (0-40% gradient) in a 1M pyridine—2M formic acid aqueous buffer from an octyl bonded silica matrix HPLC 4.6×250 mm column at room temperature and a flow rate of 0.2 ml/min.;
(h) resistant to deactivation by treatment with leucine aminopeptidase and aminopeptidase M;
(i) an amino acid composition ($\pm$15%) as based on a molecular weight of 16,000 as contained in the following table:
Asx: 11.3
Thr: 8.7
Ser: 10.3
Glx: 20.6
Pro: 5.2
Gly: 4.9
Ala: 7.2
Val: 6.0
Met: 4.8
Ile: 6.4
Leu: 18.1
Tyr: 4.4
Phe: 8.6
His: 2.8
Lys: 8.7
Arg: 7.9
Cys: 3.0
(j) providing peptide fragments upon treatment with trypsin, said fragments eluting as peaks at 3(L), 4(L), 11.5(M), 12.5(S), 14.5(M), 16(S), 17.5(S), 18(M) and 29(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient; and
(k) containing the following amino acid sequences:
  (I) ... Ala-Glu-Ile-Met-Arg ... ,
  (II) ... Lys-Tyr-Phe-Gln-Arg ... ,
  (III) ... Glx-Asx-Ser-Ile-Leu-Ala-Val-Arg ... ,
  (IV) ... Ile-Thr-Leu-Tyr-Leu-Lys ... ,
  (V) ... Thr-Leu-Met-Leu-Leu-Ala-Gln-Met-Arg . . . ,
  (IV) ... (Ser-2, Ile, Leu-2, Phe, Lys, Cys) ... ,
  (VII) ... (Asx-2, Thr-2, Ser, Glx-3, Pro, Gly, Ala, Val, Leu-3, Tyr, Lys) ... ,
  (VIII) ... (Asx, Thr-2, Ser, Glx-3, Pro, Ala, Val, Met, Ile-2, Leu-2, Phe-2, His Lys) ... .

8. A species of human leukocyte interferon designated $\beta_2$ being a homogeneous protein characterized by the following:
(a) an unblocked amino terminus;
(b) a specific activity on MDBK (bovine cells) of about $4.0 \times 10^8$ units/mg;
(c) a specific activity on Ag 1732 (human line) cells of about $2 \times 10^8$ units/mg;
(d) a molecular weight of about 16,500 ($\pm$1000) by polyacylamide gel electrophoresis;
(e) an amino sugar content of less than 1 residue per molecule;
(f) positive growth inhibition activity;
(g) eluted as a single peak at a concentration of 32% n-propanol (0-40% gradient) in a 1M pyridine-2M formic acid aqueous buffer from an octyl bonded silica matrix HPLC 4.6×250 mm column at room temperature and a flow rate of 0.2 ml/min;
(h) an amino acid composition ($\pm$15%) as based on molecular weight of 16,500 as contained in the following table:
Asx: 11.5
Thr: 9.0
Ser: 10.0
Glx: 21.9
Pro: 5.0
Gly: 5.0
Ala: 7.9
Val: 6.7
Met: 4.4
ILeu: 7.4
Leu: 18.9
Tyr: 4.6
Phe: 8.7
His: 3.0
Lys: 8.5
Arg: 8.0
Cys: 1.8
(i) providing peptide fragments upon treatment with trypsin, said fragments eluting at peaks at 3(L), 4(L), 4.2(M), 11.5(M), 12.5(S), 14.5(M), 16(S), 17.5(S), 18(M) and 29(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient;

(j) eluted as a single peak at a concentration of 66.5% n-propanol (72.5–50% gradient) in 0.1M sodium acetate aqueous buffer from a glycerol bonded silica matrix HPLC 4.6×250 mm column at room temperature and a flow rate of 0.25 ml/min.; and (k) containing the following amino acid sequences:
(I) . . . Ala-Glu-Ile-Met-Arg . . . ,
(II) . . . Lys-Tyr-Phe-Gln-Arg . . . ,
(III) . . . Glx-Asx-Ser-Ile-Leu-Ala-Val-Arg . . . ,
(IV) . . . Ile-Thr-Leu-Tyr-Leu-Lys . . . ,
(V) . . . Thr-Leu-Met-Leu-Leu-Ala-Gln-Met-Arg . . . ,
(VI) . . . (Ser-2, Ile, Leu-2, Phe, Lys, Cys) . . . ,
(VII) . . . (Asx-2, Thr-2, Ser, Glx-3, Pro, Gly, Ala, Val, Leu-3, Tyr, Lys) . . . ,
(VIII) . . . (Asx, Thr-2, Ser, Glx-3, Pro, Ala, Val, Met, Ile-2, Leu-2, Phe-2, His, Lys) . . . .

9. A species of human leukocyte interferon designated $\beta_3$ being a homogeneous protein characterized by the following:
(a) a specific activity on MDBK (bovine cells) of about $3.6 \times 10^8$ units/mg;
(b) a specific activity on AG1732 (human line) cells of about $7.6 \times 10^8$ units/mg;
(c) having a major molecular weight band of about 24,000 ($\pm 1000$) by polyacrylamide gel electrophoresis;
(d) an amino sugar content of less than 1 residue per molecule;
(e) positive growth inhibition activity;
(f) eluted as a single peak at a concentration of 32% n-propanol (0–40% gradient) in a 1M pyridine-2M formic acid aqueous buffer from an octyl bonded silica matrix HPLC 4.6×250 mm column at room temperature and a flow rate of 0.2 ml/min;
(g) an amino acid composition as contained in the following table:
Asx: 18.7
Thr: 8.3
Ser: 16.9
Glx: 35.0
Pro: 6.5
Gly: 3.5
Ala: 11.5
Val: 8.3
Met: 6.8
ILeu: 11.6
Leu: 26.0
Tyr: 6.7
Phe: 12.0
His: 4.3
Lys: 13.2
Arg: 12.1
Cys: -

(h) providing peptide fragments upon treatment with trypsin, said fragments eluting as peaks at 3(L), 4(L), 4.2(M), 4.5(S), 10(M), 12.5(S), 14(S), 14.5(M), 16(S), 18(L), 19.5(M), 27(M) and 32(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient; and (i) containing the following amino sequences:
(I) . . . Ala-Glu-Ile-Met-Arg . . . ,
(II) . . . Lys-Tyr-Phe-Gln-Arg . . . ,
(III) . . . Ile-Thr-Leu-Tyr-Leu-Lys . . . ,
(IV) . . . Thr-Leu-Met-Leu-Leu-Ala-Gln-Met-Arg . . . .

10. A species of human leukocyte interferon designated $\gamma_1$ being a homogeneous protein characterized by the following:
(a) a blocked amino terminus;
(b) a specific activity on MDBK (bovine cells) of about $2.6 \times 10^8$ units/mg;
(c) a specific activity on Ag 1732 (human line) cells of about $2 \times 10^8$ units/mg;
(d) a molecular weight of about 17,700 $\pm$ 1000 by polyacrylamide gel electrophoresis;
(e) an amino sugar content of less than 1 residue per molecule;
(f) positive growth inhibition activity;
(g) eluted as a single peak at a concentration of 31% n-propanol (0–40% gradient) in a 1M pyridine-2M formic acid aqueous buffer from an octyl bonded silica matrix HPLC 4.6×250 mm column at room temperature and a flow rate of 0.2 ml/min;
(h) resistant to deactivation by treatment with leucine aminopeptidase and aminopeptidase M;
(i) an amino acid composition ($\pm 15\%$) as based on a molecular weight of 17,700 contained in the following table:
Asx: 13.1
Thr: 8.4
Ser: 10.2
Glx: 23.9
Pro: 4.5
Gly: 5.7
Ala: 8.7
Val: 7.3
Met: 4.3
ILeu: 7.9
Leu: 20.3
Tyr: 4.8
Phe: 8.6
His: 3.7
Lys: 10.1
Arg: 8.0
Cys: 3.3

(j) providing peptide fragments upon treatment with trypsin, said fragments eluting as peaks at 3(L), 4(L), 4.2(M), 4.5(S), 5(S), 6.5(S), 11.5(S), 12.5(S), 14.5(M), 16(S), 17.5(M), 18(M) and 29(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient; and (k) containing the following amino acid sequences:
(I) . . . Ala-Glu-Ile-Met-Arg . . . ,
(II) . . . Lys-Tyr-Phe-Gln-Arg . . . ,
(III) . . . Glx-Asx-Ser-Ile-Leu-Ala-Val-Arg . . . ,
(IV) . . . Ile-Thr-Leu-Tyr-Leu-Lys . . . ,
(V) . . . Thr-Leu-Met-Leu-Leu-Ala-Gln-Met-Arg . . . ,
(VI) . . . (Ser-2, Ile, Leu-2, Phe, Lys, Cys) . . . ,
(VII) . . . (Asx-2, Thr-2, Ser, Glx-3, Pro, Gly, Ala, Val, Leu-3, Tyr, Lys) . . . ,
(VIII) . . . (Asx, Thr-2, Ser, Glx-3, Pro, Ala, Val, Met, Ile-2, Leu-2, Phe-2, His, Lys) . . . .

11. A species of human leukocyte interferon designated γ₂ being a homogeneous protein characterized by the following:
  (a) a blocked amino terminus;
  (b) a specific activity on MDBK (bovine cells) of about 4.0×10⁸ units/mg;
  (c) a specific activity on Ag 1732 (human line) cells of about 1.5×10⁸ units/mg;
  (d) a molecular weight of about 17,700 (±1000) on polyacrylamide gel electrophoresis;
  (e) an amino sugar content of less than 1 residue per molecule;
  (f) positive growth inhibition activity;
  (g) eluted as a single peak at a concentration of 32% n-propanol (0–40% gradient) in a 1M pyridine-2M formic acid aqueous buffer from an octyl bonded silica matrix HPLC 4.6×250 mm column at room temperature and a flow rate of 0.2 ml/min;
  (h) resistant to deactivation by treatment with leucine aminopeptidase and aminopeptidase M;
  (i) an amino acid composition (±15%) as based on a molecular weight of about 17,700 as contained in the following table:
  Asx: 13.3
  Thr: 9.6
  Ser: 7.8
  Glx: 25.0
  Pro: 4.8
  Gly: 5.0
  Ala: 8.1
  Val: 7.0
  Met: 3.9
  ILeu: 8.0
  Leu: 20.1
  Tyr: 4.8
  Phe: 9.0
  His: 3.3
  Lys: 10.0
  Arg: 8.5
  Cys: 2.9
  (j) providing peptide fragments upon treatment with trypsin, said fragments eluting as peaks at 3(L), 4(L), 4.2(M), 4.5(S), 5(S), 11.5(S), 12.5(S), 14.5(S), 16(S), 18(L) and 29(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient; and
  (k) containing the following amino acid sequences:
   (I) . . . Ala-Glu-Ile-Met-Arg . . . ,
   (II) . . . Lys-Tyr-Phe-Gln-Arg . . . ,
   (III) . . . Glx-Asx-Ser-Ile-Leu-Ala-Val-Arg . . . ,
   (IV) . . . Ile-Thr-Leu-Tyr-Leu-Lys . . . ,
   (V) . . . Thr-Leu-Met-Leu-Leu-Ala-Gln-Met-Arg . . . ,
   (VI) . . . (Ser-2, Ile, Leu-2, Phe, Lys, Cys) . . . ,
   (VII) . . . (Asx-2, Thr-2, Ser, Glx-3, Pro, Gly, Ala, Val, Leu-3, Tyr, Lys . . . .

12. A species of human leukocyte interferon designated γ₃ being a homogeneous protein characterized by the following:
  (a) a specific activity on MDBK (bovine cells) of about 3.5×10⁸ units/mg.;
  (b) a specific activity on AG1732 (human line) cells of about 1.5×10⁷ units/mg;
  (c) haing a major molecular weight band of about 17,200 (±1000) on polyacryamlinde gel electrophoresis;
  (d) an amino sugar content of less than 1 residue per molecule;
  (e) positive growth inhibition activity;
  (f) eluted as a single peak at a concentration of 34% n-propanol (0–40% gradient) in a 1M pyridine-2M formic acid aqueous buffer from an octyl bonded silica matrix HPLC 4.6×250 mm column at room temperature and a flow rate of 0.2 mg/min;
  (g) an amino acid composition as contained in the following table;
  Asx: 15.0
  Thr: 8.6
  Ser: 10.1
  Glx: 22.8
  Pro: 4.8
  Gly: 3.2
  Ala: 9.3
  Val: 5.5
  Met: 5.6
  ILeu: 6.8
  Leu: 20.5
  Tyr: 3.7
  Phe: 7.2
  His: 2.9
  Lys: 7.6
  Arg: 10.1
  Cys: 3.1
  (h) providing peptide fragments upon treatment with trypsin, said fragments eluting as peaks at 3(M), 4(M), 4.2(M), 11.5(M), 12.5(S), 13.5(S), 14.5(M), 16(S), 18(L), 20(S) and 32(M) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient; and
  (i) containing the following amino acid sequences:
   (I) . . . Ala-Glu-Ile-Met-Arg . . . ,
   (II) . . . Tyr-Phe-Gln-Arg . . . ,
   (IV) . . . Ile-Thr-Leu-Tyr-Leu-Lys . . . ,
   (V) . . . Thr-Leu-Met-Leu-Leu-Ala-Gln-Met-Arg . . . ,
   (VIII) . . . (Asx, Thr-2, Ser, Glx-3, Pro, Ala, Val, Met, Ile-2, Leu-2, Phe-2, His, Lys) . . . .

13. A species of human leukocyte interferon designated γ₄ being a homogeneous protein characterized by the following:
  (a) a specific activity on MDBK (bovine cells) of about 3.5×10⁸ units/mg;
  (b) a specific activity on AG1732 (human line) cells of about 4.0×10⁸ units/mg;
  (c) a molecular weight of about 21,000 (±1000) on polyacrylamide gel electrophoresis;
  (d) an amino sugar content of less than 1 residue per molecule;
  (e) positive growth inhibition activity;
  (f) eluted as a single peak at a concentration of 35% n-propanol (0–40% gradient) in a 1M pyridine-2M formic acid aqueous buffer from a octyl bonded silica matrix HPLC 4.6×250 mm column at room temperature and a flow rate of 0.2 ml/min;
  (g) an amino acid composition as contained in the following table:
  Asx: 17.9

Thr: 7.3
Ser: 13.5
Glx: 27.0
Pro: 6.5
Gly: 4.8
Ala: 10.4
Val: 7.9
Met: 4.9
ILeu: 9.7
Leu: 24.1
Tyr: 5.0
Phe: 9.1
His: 3.8
Lys: 12.3
Arg: 8.5
Cys: 4.1 and (h) containing the following amino acid sequences:
 (I) . . . Ala-Glu-Ile-Met-Arg . . . ,
 (II) . . . Tyr-Phe-Gln-Arg . . . ,
 (III) . . . Ile, Thr-Leu-Tyr-Leu-Lys . . . ,
 (IV) . . . Thr-Leu-Met-Leu-Leu-Ala-Gln-Met-Arg . . . .

14. A species of human leukocyte interferon designated γ5 being a homogenous protein characterized by the following:
 (a) a specific activity on MDBK (bovine cells) of about $0.9 \times 10^8$ units/mg;
 (b) a specific activity on AG1732 (human line) cells of about $2 \times 10^6$ units/mg;
 (c) having a major molecular weight band of about 16,500 ($\pm$1000) on polyacrylamide gel electrophoresis;
 (d) an amino sugar content of less than 1 residue per molecule;
 (e) positive growth inhibition activity;
 (f) eluted as a single peak at a concentration of 35.5% no-propanol (0–40% gradient) in a 1M pyridine-2M formic acid aqueous buffer from an octyl bonded silica matrix HPLC 4.5×250 mm column at room temperature and a flow rate of 0.2 ml/min;
 (g) an amino acid composition as contained in the following table:
  Asx: 13.8
  Thr: 7.6
  Ser: 9.0
  Glx: 20.8
  Pro: 4.2
  Gly: 4.0
  Ala: 9.3
  Val: 5.1
  Met: 4.7
  ILeu: 6.6
  Leu: 19.6
  Tyr: 3.6
  Phe: 6.4
  His: 2.8
  Lys: 12.0
  Arg: 9.0
  Cys: 2.3
 (h) providing peptide fragments upon treatment with trypsin, said fragments eluting as peaks at 3(L), 4(L), 4.2(M), 4.5(M), 7(S), 7.5(S), 10(S), 11.5(L), 12.5(S), 14(S), 14.5(M), 16(S), 18(L), 24.5(S), 25.5(S) and 32(S) % n-propanol when the reaction media is passed through an octyl bonded silica matrix 10μ particle size HPLC 4.6×250 mm column at room temperature using a 0.03M pyridine-0.1M formic acid aqueous buffer (pH 3) at a flow rate of 0.5 ml/min. with a 1 hour 0 to 40% n-propanol gradient.

and (i) containing the following amino acid sequences:
 (I) . . . Ala-Glu-Ile-Met-Arg . . . ,
 (II) . . . Tyr-Phe-Gln-Arg . . . ,
 (III) . . . Ile, Thr-Leu-Tyr-Leu-Lys . . . ,
 (IV) . . . Thr-Leu-Met-Leu-Leu-Ala-Gln-Met-Arg . . . .

* * * * *

REEXAMINATION CERTIFICATE (2816th)

United States Patent [19]

Pestka et al.

[11] B1 4,503,035

[45] Certificate Issued Mar. 19, 1996

[54] PROTEIN PURIFICATION PROCESS AND PRODUCT

[75] Inventors: Sidney Pestka, North Caldwell, N.J.; Menachem Rubinstein, Rimon, Israel

[73] Assignee: Hoffmann-La Roche, Inc., Nutley, N.J.

Reexamination Request:
No. 90/002,881, Nov. 20, 1992

Reexamination Certificate for:
Patent No.: 4,503,035
Issued: Mar. 5, 1985
Appl. No.: 465,979
Filed: Feb. 14, 1983

Related U.S. Application Data

[60] Continuation of Ser. No. 247,442, Mar. 25, 1981, abandoned, which is a division of Ser. No. 167,165, Jul. 9, 1980, Pat. No. 4,289,690, which is a continuation-in-part of Ser. No. 106,644, Dec. 26, 1979, abandoned, which is a continuation-in-part of Ser. No. 77,710, Sep. 21, 1979, abandoned, which is a continuation-in-part of Ser. No. 62,374, Jul. 31, 1979, abandoned, which is a continuation-in-part of Ser. No. 963,257, Nov. 24, 1978, abandoned.

[51] Int. Cl.⁶ ............... A61K 38/21; C12P 21/02; C07K 1/00; C07K 1/16; C07K 14/56
[52] U.S. Cl. ............ 424/85.7; 425/69.51; 425/70.5; 425/811; 530/351; 530/417; 530/828; 530/829; 530/854; 930/10; 930/142
[58] Field of Search ................... 530/351, 417, 530/828, 829, 854; 424/85.7, 85.5, 85.6; 930/10, 142; 435/70.5, 811, 69.51

[56] References Cited

U.S. PATENT DOCUMENTS 4,534,906  8/1985  Johnston et al. ............... 530/351

OTHER PUBLICATIONS

Rubinstein et al., *Science* 202:1289–1290 (Dec. 22, 1978).
Rubinstein et al., *PNAS USA* 76:640–644 (Feb. 1979).
*Sloan–Kettering Second International Workshop on Interferons* (Apr. 22–24, 1979).
Slides Accompanying Dr. Lin's Apr. 23, 1979 Workshop (FTC Lin Exhibits 22–27).
Lin et al, *Methods in Enzymology* 78:481–487 (1981).
Stewart et al, *Virology* 67:68–73 (1975).
1979 Annual Report of the Sloan–Kettering Institute for Cancer Research 280–281 (1980).
Lin et al, *J. Gen. Virology* 39:125–130 (1978).
Stewart et al *PNAS USA* 74:4200–4204 (Oct. 1977).
Salit et al, *Archives of Virology* 63:133–142 (Feb. 1980).
Stewart et al, *Nature* 262:300–302 (Jul. 1976).
Abstract 202, 78th Annual Meeting of the American Society for Microbiology 246 (May 1978).
Poster Exhibits accompanying Sloan–Kettering May 1978 A–S–M–presentation (Lin and Stewart FTC Exhibits 2–C, 2–J, 2–M, 2–N, 2–O).
Abstract No. 953, Annual Meeting of the American Society of Biological Chemists (Jun. 1978), *Fed. Proc. Fed. Am. Soc. Exp. Biol.* 37:1441 (1978).
Poster Exhibits accompanying Sloan–Kettering, Jun. 1978. ASBC meeting (Lin and Stewart FTC Exhibits 2–C, 2–M).
De Maeyer–Guignard et al., *Nature* 271:622–625 (Feb. 16, 1978).
De Maeyer–Grignard et al, *PNAS USA* 74:3787–3790 (Sep. 1977).
1978 Annual Report of Sloan–Kettering Institute for Cancer Research 225–226 (1979).
Stewart et al. Abstracts of IVth International Congress for Virology, The Hague (Aug.–Sep. 1978).
Zoon et al, *Science* 207:527–528 (Feb. 1, 1980).
Zoon et al, *J. Interferon Research* 2:253–260 (1982).

*Primary Examiner*—James Martinell

[57] ABSTRACT

An improved process for purifying proteins, particularly proteins having molecular weights in excess of 12,000 involves novel applications of high performance liquid chromatography on a preparative scale to provide homogeneous end product in excellent yield. In an embodiment of the process, human interferon is produced as a homogeneous protein.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–14 is confirmed.

New claims 15–22 are added and determined to be patentable.

*15. Human leukocyte interferon as a homogeneous protein species having a specific activity of from $0.9 \times 10^8 – 4 \times 10^8$ Units/mg of protein when assayed on the MDBK bovine cell line and from $2 \times 10^6 – 4 \times 10^8$ Units/mg of protein when assayed on the AG 1732 human cell line.*

*16. The homogeneous human interferon of claim 15 which is a human leukocyte interferon characterized by containing the following amino acid sequences:*

*(I) ... Ala-Glu-Ile-Met-Arg ...*

*(II) ... Tyr-Phe-Gln-Arg ...*

*(III) ... Ile-Thr-Leu-Tyr-Leu-Lys ..., and*

*(IV) ... Thr-Leu-Met-Leu-Leu- Ala-Gln-Met-Arg ....*

*17. Human leukocyte interferon as a mixture of human leukocyte interferon species according to claim 15.*

*18. A pharmaceutical preparation suitable for parenteral administration for treatment of viral and neoplastic disease states said preparation comprising a minor, effective amount of at least one human leukocyte interferon species according to claim 15 and a major amount of a conventional pharmaceutical parenteral carrier material.*

*19. Human leukocyte interferon as a homogeneous protein species having a specific activity of from $2.6 \times 10^8 – 4 \times 10^8$ Units/mg of protein when assayed on the MDBK bovine cell line and from $1.5 \times 10^8 – 4 \times 10^8$ Units/mg of protein when assayed on the AG 1732 human cell line.*

*20. The homogeneous human interferon of claim 19 which is a human leukocyte interferon characterized by containing the following amino acid sequences:*

*(I) ... Ala-Glu-Ile-Met-Arg ...*

*(II) ... Tyr-Phe-Gln-Arg ...*

*(III) ... Ile-Thr-Leu-Tyr-Leu-Lys ..., and*

*(IV) ... Thr-Leu-Met-Leu-Leu- Ala-Gln-Met-Arg ....*

*21. Human leukocyte interferon as a mixture of human leukocyte interferon species according to claim 19.*

*22. A pharmaceutical preparation suitable for parenteral administration for treatment of viral and neoplastic disease states said preparation comprising a minor, effective amount of at least one human leukocyte interferon species according to claim 19 and a major amount of a conventional pharmaceutical parenteral carrier material.*

\* \* \* \* \*